(12) United States Patent
Cunningham et al.

(10) Patent No.: US 8,303,586 B2
(45) Date of Patent: *Nov. 6, 2012

(54) SPRING LOADED RECIPROCATING TISSUE CUTTING MECHANISM IN A FORCEPS-STYLE ELECTROSURGICAL INSTRUMENT

(75) Inventors: James S. Cunningham, Boulder, CO (US); Dennis J. Harvilla, Lafayette, CO (US)

(73) Assignee: Covidien AG (CH)

( * ) Notice: Subject to any disclaimer, the term of this patent is extended or adjusted under 35 U.S.C. 154(b) by 941 days.

This patent is subject to a terminal disclaimer.

(21) Appl. No.: 12/368,815

(22) Filed: Feb. 10, 2009

(65) Prior Publication Data

US 2009/0149854 A1    Jun. 11, 2009

Related U.S. Application Data

(63) Continuation of application No. 11/242,488, filed on Oct. 3, 2005, now Pat. No. 7,500,975, which is a continuation-in-part of application No. 10/991,157, filed on Nov. 17, 2004, now Pat. No. 7,131,970.

(60) Provisional application No. 60/523,387, filed on Nov. 19, 2003, provisional application No. 60/616,972, filed on Oct. 8, 2004, provisional application No. 60/616,968, filed on Oct. 8, 2004.

(51) Int. Cl.
*A61B 18/14* (2006.01)

(52) U.S. Cl. ............................................. 606/51; 606/45
(58) Field of Classification Search .............. 606/48–52, 606/205–207
See application file for complete search history.

(56) References Cited

U.S. PATENT DOCUMENTS

| 371,664 A | 10/1887 | Brannan et al. |
|---|---|---|
| 702,472 A | 6/1902 | Pignolet |
| 728,883 A | 5/1903 | Downes |
| 1,586,645 A | 6/1926 | Bierman |
| 1,813,902 A | 7/1931 | Bovie |
| 1,822,330 A | 9/1931 | Ainslie |
| 1,852,542 A | 4/1932 | Sovatkin |

(Continued)

FOREIGN PATENT DOCUMENTS

CA       2104423       2/1994

(Continued)

OTHER PUBLICATIONS

Michael Choti, "Abdominoperineal Resection with the LigaSure Vessel Sealing System and LigaSure Atlas 20 cm Open Instrument" ; Innovations That Work, Jun. 2003.

(Continued)

*Primary Examiner* — Michael Peffley

(57) ABSTRACT

Open electrosurgical forceps for sealing tissue which include a pair of first and second shaft portions each having a jaw member disposed at a distal end thereof. Each of the jaw members includes an electrically conductive sealing surface which communicates electrosurgical energy through tissue held therebetween with at least one of the jaw members including a knife slot defined along a length thereof. The knife slot is dimensioned to reciprocate a knife blade therefrom. The forceps also have a cutting mechanism which selectively actuates the knife blade from a first position wherein the knife blade is disposed at least substantially entirely within the knife slot of the jaw member to at least one subsequent position wherein the knife blade is at least partially deployed from the knife slot of the jaw member. The knife blade is displaceable in a direction transverse to a longitudinal axis of the forceps.

15 Claims, 16 Drawing Sheets

U.S. PATENT DOCUMENTS

| | | |
|---|---|---|
| 2,002,594 A | 5/1935 | Wappler et al. |
| 2,011,169 A | 8/1935 | Wappler |
| 2,031,682 A | 2/1936 | Wappler et al. |
| 2,054,149 A | 9/1936 | Wappler |
| 2,176,479 A | 10/1939 | Willis |
| 2,305,156 A | 4/1941 | Grubel |
| 2,279,753 A | 4/1942 | Knopp |
| 2,327,353 A | 8/1943 | Karle |
| 2,632,661 A | 8/1948 | Cristofv |
| 2,668,538 A | 2/1954 | Baker |
| 2,796,065 A | 6/1957 | Kapp |
| 3,073,311 A | 1/1963 | Tibbs et al. |
| 3,372,288 A | 3/1968 | Wigington |
| 3,459,187 A | 8/1969 | Pallotta |
| 3,643,663 A | 2/1972 | Sutter |
| 3,648,001 A | 3/1972 | Anderson et al. |
| 3,651,811 A | 3/1972 | Hildebrandt et al. |
| 3,678,229 A | 7/1972 | Osika |
| 3,720,896 A | 3/1973 | Beierlein |
| 3,763,726 A | 10/1973 | Hildebrand |
| 3,779,918 A | 12/1973 | Ikeda et al. |
| 3,801,766 A | 4/1974 | Morrison, Jr. |
| 3,862,630 A | 1/1975 | Balamuth |
| 3,863,339 A | 2/1975 | Reaney et al. |
| 3,866,610 A | 2/1975 | Kletschka |
| 3,911,766 A | 10/1975 | Fridolph et al. |
| 3,920,021 A | 11/1975 | Hiltebrandt |
| 3,921,641 A | 11/1975 | Hulka |
| 3,938,527 A | 2/1976 | Rioux et al. |
| 3,952,749 A | 4/1976 | Fridolph et al. |
| 3,970,088 A | 7/1976 | Morrison |
| 3,987,795 A | 10/1976 | Morrison |
| 4,005,714 A | 2/1977 | Hiltebrandt |
| 4,016,881 A | 4/1977 | Rioux et al. |
| 4,041,952 A | 8/1977 | Morrison, Jr. et al. |
| 4,043,342 A | 8/1977 | Morrison, Jr. |
| 4,074,718 A | 2/1978 | Morrison, Jr. |
| 4,076,028 A | 2/1978 | Simmons |
| 4,080,820 A | 3/1978 | Allen |
| 4,088,134 A | 5/1978 | Mazzariello |
| 4,112,950 A | 9/1978 | Pike |
| 4,127,222 A | 11/1978 | Adams |
| 4,128,099 A | 12/1978 | Bauer |
| 4,165,746 A | 8/1979 | Burgin |
| 4,187,420 A | 2/1980 | Piber |
| 4,233,734 A | 11/1980 | Bies |
| 4,236,470 A | 12/1980 | Stenson |
| 4,300,564 A | 11/1981 | Furihata |
| 4,311,145 A | 1/1982 | Esty et al. |
| D263,020 S | 2/1982 | Rau, III |
| 4,370,980 A | 2/1983 | Lottick |
| 4,375,218 A | 3/1983 | DiGeronimo |
| 4,416,276 A | 11/1983 | Newton et al. |
| 4,418,692 A | 12/1983 | Guay |
| 4,443,935 A | 4/1984 | Zamba et al. |
| 4,452,246 A | 6/1984 | Bader et al. |
| 4,470,786 A | 9/1984 | Sano et al. |
| 4,492,231 A | 1/1985 | Auth |
| 4,493,320 A | 1/1985 | Treat |
| 4,503,855 A | 3/1985 | Maslanka |
| 4,506,669 A | 3/1985 | Blake, III |
| 4,509,518 A | 4/1985 | McGarry et al. |
| 4,552,143 A | 11/1985 | Lottick |
| 4,574,804 A | 3/1986 | Kurwa |
| 4,597,379 A | 7/1986 | Kihn et al. |
| 4,600,007 A | 7/1986 | Lahodny et al. |
| 4,624,254 A | 11/1986 | McGarry et al. |
| 4,655,215 A | 4/1987 | Pike |
| 4,655,216 A * | 4/1987 | Tischer .................. 606/51 |
| 4,657,016 A | 4/1987 | Garito et al. |
| 4,662,372 A | 5/1987 | Sharkany et al. |
| 4,671,274 A | 6/1987 | Sorochenko |
| 4,685,459 A | 8/1987 | Xoch et al. |
| 4,733,662 A | 3/1988 | DeSatnick et al. |
| D295,893 S | 5/1988 | Sharkany et al. |
| D295,894 S | 5/1988 | Sharkany et al. |
| 4,754,892 A | 7/1988 | Retief |
| 4,763,669 A | 8/1988 | Jaeger |
| 4,827,929 A | 5/1989 | Hodge |
| 4,829,313 A | 5/1989 | Taggart |
| 4,846,171 A | 7/1989 | Kauphusman et al. |
| 4,887,612 A | 12/1989 | Esser et al. |
| 4,938,761 A | 7/1990 | Ensslin |
| 4,947,009 A | 8/1990 | Osika et al. |
| 4,985,030 A | 1/1991 | Melzer et al. |
| 5,007,908 A | 4/1991 | Rydell |
| 5,026,370 A | 6/1991 | Lottick |
| 5,026,371 A | 6/1991 | Rydell et al. |
| 5,035,695 A | 7/1991 | Weber, Jr. et al. |
| 5,037,433 A | 8/1991 | Wilk et al. |
| 5,042,707 A | 8/1991 | Taheri |
| 5,047,046 A | 9/1991 | Bodoia |
| 5,078,716 A | 1/1992 | Doll |
| 5,084,057 A | 1/1992 | Green et al. |
| 5,085,659 A | 2/1992 | Rydell |
| 5,099,840 A | 3/1992 | Goble et al. |
| 5,100,430 A | 3/1992 | Avellanet et al. |
| 5,108,392 A | 4/1992 | Spingler |
| 5,112,343 A | 5/1992 | Thornton |
| 5,116,332 A | 5/1992 | Lottick |
| 5,147,357 A | 9/1992 | Rose et al. |
| 5,151,102 A | 9/1992 | Kamiyama et al. |
| 5,151,978 A | 9/1992 | Bronikowski et al. |
| 5,176,695 A | 1/1993 | Dulebohn |
| 5,190,541 A | 3/1993 | Abele et al. |
| 5,196,009 A | 3/1993 | Kirwan, Jr. |
| 5,197,964 A | 3/1993 | Parins |
| 5,209,747 A | 5/1993 | Knoepfler |
| 5,211,655 A | 5/1993 | Hasson |
| 5,215,101 A | 6/1993 | Jacobs et al. |
| 5,217,457 A | 6/1993 | Delahuerga et al. |
| 5,217,458 A | 6/1993 | Parins |
| 5,217,460 A | 6/1993 | Knoepfler |
| 5,219,354 A | 6/1993 | Choudhury et al. |
| 5,244,462 A | 9/1993 | Delahuerga et al. |
| 5,250,047 A | 10/1993 | Rydell |
| 5,250,063 A | 10/1993 | Abidin et al. |
| 5,258,001 A | 11/1993 | Corman |
| 5,258,006 A | 11/1993 | Rydell et al. |
| 5,261,918 A | 11/1993 | Phillips et al. |
| 5,275,615 A | 1/1994 | Rose |
| 5,277,201 A | 1/1994 | Stern |
| 5,282,799 A | 2/1994 | Rydell |
| 5,282,800 A | 2/1994 | Foshee et al. |
| 5,282,826 A | 2/1994 | Quadri |
| 5,290,286 A | 3/1994 | Parins |
| 5,300,082 A | 4/1994 | Sharpe et al. |
| 5,304,203 A | 4/1994 | El-Mallawany et al. |
| 5,308,353 A | 5/1994 | Beurrier |
| 5,308,357 A | 5/1994 | Lichtman |
| 5,313,027 A | 5/1994 | Inoue et al. |
| 5,314,445 A | 5/1994 | Degwitz et al. |
| 5,318,589 A | 6/1994 | Lichtman |
| 5,324,289 A | 6/1994 | Eggers |
| D348,930 S | 7/1994 | Olson |
| 5,326,806 A | 7/1994 | Yokoshima et al. |
| 5,330,471 A | 7/1994 | Eggers |
| 5,330,502 A | 7/1994 | Hassler et al. |
| 5,334,183 A | 8/1994 | Wuchinich |
| 5,334,215 A | 8/1994 | Chen |
| 5,336,220 A | 8/1994 | Ryan et al. |
| 5,336,221 A | 8/1994 | Anderson |
| 5,342,359 A | 8/1994 | Rydell |
| 5,342,381 A | 8/1994 | Tidemand |
| 5,342,393 A | 8/1994 | Stack |
| 5,344,424 A | 9/1994 | Roberts et al. |
| 5,350,391 A | 9/1994 | Iacovelli |
| 5,352,222 A | 10/1994 | Rydell |
| 5,354,271 A | 10/1994 | Voda |
| 5,356,408 A | 10/1994 | Rydell |
| 5,366,477 A | 11/1994 | LeMarie, III et al. |
| 5,368,600 A | 11/1994 | Failla et al. |
| 5,374,277 A | 12/1994 | Hassler |
| 5,376,089 A | 12/1994 | Smith |
| 5,383,875 A | 1/1995 | Bays et al. |
| 5,383,897 A | 1/1995 | Wholey |
| 5,389,098 A | 2/1995 | Tsuruta et al. |

| Patent | Kind | Date | Inventor |
|---|---|---|---|
| 5,389,103 | A | 2/1995 | Melzer et al. |
| 5,389,104 | A | 2/1995 | Hahnen et al. |
| 5,391,166 | A | 2/1995 | Eggers |
| 5,391,183 | A | 2/1995 | Janzen et al. |
| 5,396,900 | A | 3/1995 | Slater et al. |
| 5,403,312 | A | 4/1995 | Yates et al. |
| 5,403,342 | A | 4/1995 | Tovey et al. |
| 5,405,344 | A | 4/1995 | Williamson et al. |
| 5,409,763 | A | 4/1995 | Serizawa et al. |
| 5,411,519 | A | 5/1995 | Tovey et al. |
| 5,411,520 | A | 5/1995 | Nash et al. |
| 5,413,571 | A | 5/1995 | Katsaros et al. |
| 5,415,656 | A | 5/1995 | Tihon et al. |
| 5,415,657 | A | 5/1995 | Taymor-Luria |
| 5,422,567 | A | 6/1995 | Matsunaga |
| 5,423,810 | A | 6/1995 | Goble et al. |
| 5,425,690 | A | 6/1995 | Chang |
| 5,425,739 | A | 6/1995 | Jessen |
| 5,429,616 | A | 7/1995 | Schaffer |
| 5,431,672 | A | 7/1995 | Cote et al. |
| 5,431,674 | A | 7/1995 | Basile et al. |
| 5,437,292 | A | 8/1995 | Kipshidze et al. |
| 5,438,302 | A | 8/1995 | Goble |
| 5,439,478 | A | 8/1995 | Palmer |
| 5,441,517 | A | 8/1995 | Kensey et al. |
| 5,443,463 | A | 8/1995 | Stern et al. |
| 5,443,464 | A | 8/1995 | Russell et al. |
| 5,443,480 | A | 8/1995 | Jacobs et al. |
| 5,445,638 | A | 8/1995 | Rydell et al. |
| 5,445,658 | A | 8/1995 | Durrfeld et al. |
| 5,449,480 | A | 9/1995 | Kuriya et al. |
| 5,451,224 | A | 9/1995 | Goble et al. |
| 5,454,823 | A | 10/1995 | Richardson et al. |
| 5,454,827 | A | 10/1995 | Aust et al. |
| 5,456,684 | A | 10/1995 | Schmidt et al. |
| 5,458,598 | A | 10/1995 | Feinberg et al. |
| 5,460,629 | A | 10/1995 | Shlain et al. |
| 5,461,765 | A | 10/1995 | Linden et al. |
| 5,462,546 | A | 10/1995 | Rydell |
| 5,472,442 | A | 12/1995 | Klicek |
| 5,472,443 | A | 12/1995 | Cordis et al. |
| 5,478,351 | A | 12/1995 | Meade et al. |
| 5,480,406 | A | 1/1996 | Nolan et al. |
| 5,480,409 | A | 1/1996 | Riza |
| 5,484,436 | A | 1/1996 | Eggers et al. |
| 5,496,312 | A | 3/1996 | Klicek |
| 5,496,317 | A | 3/1996 | Goble et al. |
| 5,496,347 | A | 3/1996 | Hashiguchi et al. |
| 5,499,997 | A | 3/1996 | Sharpe et al. |
| 5,509,922 | A | 4/1996 | Aranyi et al. |
| 5,512,721 | A | 4/1996 | Young et al. |
| 5,514,134 | A | 5/1996 | Rydell et al. |
| 5,527,313 | A | 6/1996 | Scott et al. |
| 5,528,833 | A | 6/1996 | Sakuma |
| 5,529,067 | A | 6/1996 | Larsen et al. |
| 5,531,744 | A | 7/1996 | Nardella et al. |
| 5,536,251 | A | 7/1996 | Evard et al. |
| 5,540,684 | A | 7/1996 | Hassler, Jr. |
| 5,540,685 | A | 7/1996 | Parins et al. |
| 5,540,706 | A | 7/1996 | Aust et al. |
| 5,540,715 | A | 7/1996 | Katsaros et al. |
| 5,542,945 | A | 8/1996 | Fritzsch |
| 5,558,671 | A | 9/1996 | Yates |
| 5,558,672 | A | 9/1996 | Edwards et al. |
| 5,562,619 | A | 10/1996 | Mirarchi et al. |
| 5,562,699 | A | 10/1996 | Heimberger et al. |
| 5,562,720 | A | 10/1996 | Stern et al. |
| 5,564,615 | A | 10/1996 | Bishop et al. |
| 5,569,241 | A | 10/1996 | Edwardds et al. |
| 5,569,243 | A | 10/1996 | Kortenbach et al. |
| 5,571,100 | A | 11/1996 | Goble et al. |
| 5,573,424 | A | 11/1996 | Poppe |
| 5,573,534 | A | 11/1996 | Stone |
| 5,573,535 | A | 11/1996 | Viklund |
| 5,575,799 | A | 11/1996 | Bolanos et al. |
| 5,575,805 | A | 11/1996 | Li |
| 5,578,052 | A | 11/1996 | Koros et al. |
| 5,579,781 | A | 12/1996 | Cooke |
| 5,582,611 | A | 12/1996 | Tsuruta et al. |
| 5,582,617 | A | 12/1996 | Klieman et al. |
| 5,585,896 | A | 12/1996 | Yamazaki et al. |
| 5,590,570 | A | 1/1997 | LeMaire, III et al. |
| 5,591,181 | A | 1/1997 | Stone et al. |
| 5,597,107 | A | 1/1997 | Knodel et al. |
| 5,601,224 | A | 2/1997 | Bishop et al. |
| 5,601,601 | A | 2/1997 | Tal et al. |
| 5,601,641 | A | 2/1997 | Stephens |
| 5,603,711 | A | 2/1997 | Parins et al. |
| 5,603,723 | A | 2/1997 | Aranyi et al. |
| 5,611,798 | A | 3/1997 | Eggers |
| 5,611,808 | A | 3/1997 | Hossain et al. |
| 5,611,813 | A | 3/1997 | Lichtman |
| 5,620,415 | A | 4/1997 | Lucey et al. |
| 5,620,453 | A | 4/1997 | Nallakrishnan |
| 5,620,459 | A | 4/1997 | Lichtman |
| 5,624,452 | A | 4/1997 | Yates |
| 5,626,578 | A | 5/1997 | Tihon |
| 5,626,609 | A | 5/1997 | Zvenyatsky et al. |
| 5,630,833 | A | 5/1997 | Katsaros et al. |
| 5,637,110 | A | 6/1997 | Pennybacker et al. |
| 5,638,003 | A | 6/1997 | Hall |
| 5,643,294 | A | 7/1997 | Tovey et al. |
| 5,647,869 | A | 7/1997 | Goble et al. |
| 5,647,871 | A | 7/1997 | Levine et al. |
| 5,649,959 | A | 7/1997 | Hannam et al. |
| 5,655,650 | A | 8/1997 | Naitou |
| 5,658,281 | A | 8/1997 | Heard |
| D384,413 | S | 9/1997 | Zlock et al. |
| 5,662,667 | A | 9/1997 | Knodel |
| 5,665,100 | A | 9/1997 | Yoon |
| 5,667,526 | A | 9/1997 | Levin |
| 5,674,220 | A | 10/1997 | Fox et al. |
| 5,674,229 | A | 10/1997 | Tovey et al. |
| 5,681,282 | A | 10/1997 | Eggers et al. |
| 5,688,270 | A | 11/1997 | Yates et al. |
| 5,690,652 | A | 11/1997 | Wurster et al. |
| 5,690,653 | A | 11/1997 | Richardson et al. |
| 5,693,051 | A | 12/1997 | Schulze et al. |
| 5,693,920 | A | 12/1997 | Maeda |
| 5,695,522 | A | 12/1997 | LeMaire, III et al. |
| 5,700,261 | A | 12/1997 | Brinkerhoff |
| 5,700,270 | A | 12/1997 | Peyser et al. |
| 5,702,390 | A | 12/1997 | Austin et al. |
| 5,707,369 | A | 1/1998 | Vaitekunas et al. |
| 5,709,680 | A | 1/1998 | Yates et al. |
| 5,716,366 | A | 2/1998 | Yates |
| 5,720,744 | A | 2/1998 | Eggleston et al. |
| 5,722,421 | A | 3/1998 | Francese et al. |
| 5,725,536 | A | 3/1998 | Oberlin et al. |
| 5,727,428 | A | 3/1998 | LeMaire, III et al. |
| 5,735,848 | A | 4/1998 | Yates et al. |
| 5,743,906 | A | 4/1998 | Parins et al. |
| 5,752,973 | A | 5/1998 | Kieturakis |
| 5,755,717 | A | 5/1998 | Yates et al. |
| 5,759,188 | A | 6/1998 | Yoon |
| 5,766,130 | A | 6/1998 | Selmonosky |
| 5,766,166 | A | 6/1998 | Hooven |
| 5,766,170 | A | 6/1998 | Eggers |
| 5,766,196 | A | 6/1998 | Griffiths |
| 5,769,849 | A | 6/1998 | Eggers |
| 5,772,655 | A | 6/1998 | Bauer et al. |
| 5,772,670 | A | 6/1998 | Brosa |
| 5,776,128 | A | 7/1998 | Eggers |
| 5,776,130 | A | 7/1998 | Buysse et al. |
| 5,779,646 | A | 7/1998 | Koblish et al. |
| 5,779,701 | A | 7/1998 | McBrayer et al. |
| H1745 | H | 8/1998 | Paraschac |
| 5,792,137 | A | 8/1998 | Carr et al. |
| 5,792,165 | A | 8/1998 | Klieman et al. |
| 5,792,177 | A | 8/1998 | Kaseda |
| 5,797,537 | A | 8/1998 | Oberlin et al. |
| 5,797,927 | A | 8/1998 | Yoon |
| 5,797,938 | A | 8/1998 | Paraschac et al. |
| 5,797,941 | A * | 8/1998 | Schulze et al. ................ 606/171 |
| 5,797,958 | A | 8/1998 | Yoon |
| 5,800,449 | A | 9/1998 | Wales |
| 5,807,393 | A | 9/1998 | Williamson, IV et al. |
| 5,810,764 | A | 9/1998 | Eggers et al. |

| | | | | | |
|---|---|---|---|---|---|
| 5,810,805 A | 9/1998 | Sutcu et al. | 6,059,782 A | 5/2000 | Novak et al. |
| 5,810,808 A | 9/1998 | Eggers | 6,066,139 A | 5/2000 | Ryan et al. |
| 5,810,811 A | 9/1998 | Yates et al. | 6,074,386 A | 6/2000 | Goble et al. |
| 5,810,877 A | 9/1998 | Roth et al. | 6,077,287 A | 6/2000 | Taylor et al. |
| 5,814,043 A | 9/1998 | Shapeton | 6,080,180 A | 6/2000 | Yoon et al. |
| 5,814,054 A | 9/1998 | Kortenbach et al. | RE36,795 E | 7/2000 | Rydell |
| 5,817,093 A | 10/1998 | Williamson, IV et al. | 6,083,223 A | 7/2000 | Baker |
| 5,817,119 A | 10/1998 | Klieman et al. | 6,086,586 A | 7/2000 | Hooven |
| 5,820,630 A | 10/1998 | Lind | 6,086,601 A | 7/2000 | Yoon |
| 5,824,978 A | 10/1998 | Karasik et al. | 6,090,107 A | 7/2000 | Borgmeier et al. |
| 5,827,271 A | 10/1998 | Buysse et al. | 6,096,037 A | 8/2000 | Mulier et al. |
| 5,827,279 A | 10/1998 | Hughett et al. | 6,099,550 A | 8/2000 | Yoon |
| 5,827,281 A | 10/1998 | Levin | 6,102,909 A | 8/2000 | Chen et al. |
| 5,827,323 A | 10/1998 | Klieman et al. | 6,106,542 A | 8/2000 | Toybin et al. |
| 5,827,548 A | 10/1998 | Lavallee et al. | 6,110,171 A | 8/2000 | Rydell |
| 5,833,690 A | 11/1998 | Yates et al. | 6,113,596 A | 9/2000 | Hooven et al. |
| 5,843,080 A | 12/1998 | Fleenor et al. | 6,113,598 A | 9/2000 | Baker |
| 5,849,022 A | 12/1998 | Sakashita et al. | 6,117,158 A | 9/2000 | Measamer et al. |
| 5,853,412 A | 12/1998 | Mayenberger | 6,122,549 A | 9/2000 | Sharkey et al. |
| 5,859,527 A | 1/1999 | Cook | 6,123,701 A | 9/2000 | Nezhat |
| 5,860,976 A | 1/1999 | Billings et al. | H1904 H | 10/2000 | Yates et al. |
| 5,876,401 A | 3/1999 | Schulze et al. | 6,126,658 A | 10/2000 | Baker |
| 5,876,412 A | 3/1999 | Piraka | 6,126,665 A | 10/2000 | Yoon |
| 5,882,567 A | 3/1999 | Cavallaro et al. | 6,139,563 A | 10/2000 | Cosgrove, III et al. |
| 5,891,141 A | 4/1999 | Rydell | 6,143,005 A | 11/2000 | Yoon et al. |
| 5,891,142 A | 4/1999 | Eggers et al. | 6,152,923 A | 11/2000 | Ryan |
| 5,893,863 A | 4/1999 | Yoon | 6,162,220 A | 12/2000 | Nezhat |
| 5,893,875 A | 4/1999 | O'Connor et al. | 6,171,316 B1 | 1/2001 | Kovac et al. |
| 5,893,877 A | 4/1999 | Gampp, Jr. et al. | 6,174,309 B1 | 1/2001 | Wrublewski et al. |
| 5,897,563 A | 4/1999 | Yoon et al. | 6,178,628 B1 | 1/2001 | Clemens et al. |
| 5,902,301 A | 5/1999 | Olig | 6,179,834 B1 | 1/2001 | Buysse et al. |
| 5,906,630 A | 5/1999 | Anderhub et al. | 6,179,837 B1 | 1/2001 | Hooven |
| 5,908,420 A | 6/1999 | Parins et al. | 6,183,467 B1 | 2/2001 | Shapeton et al. |
| 5,908,432 A | 6/1999 | Pan | 6,187,003 B1 | 2/2001 | Buysse et al. |
| 5,911,719 A | 6/1999 | Eggers | 6,190,386 B1 | 2/2001 | Rydell |
| 5,913,874 A | 6/1999 | Berns et al. | 6,190,400 B1 | 2/2001 | VanDeMoer et al. |
| 5,921,916 A | 7/1999 | Aeikens et al. | 6,193,718 B1 | 2/2001 | Kortenbach et al. |
| 5,921,984 A | 7/1999 | Sutcu et al. | 6,206,876 B1 | 3/2001 | Levine et al. |
| 5,925,043 A | 7/1999 | Kumar et al. | 6,206,877 B1 | 3/2001 | Kese et al. |
| 5,928,136 A | 7/1999 | Barry | 6,206,893 B1 | 3/2001 | Klein et al. |
| 5,935,126 A | 8/1999 | Riza | 6,214,028 B1 | 4/2001 | Yoon et al. |
| 5,941,869 A | 8/1999 | Patterson et al. | 6,217,602 B1 | 4/2001 | Redmon |
| 5,944,718 A | 8/1999 | Austin et al. | 6,217,615 B1 | 4/2001 | Sioshansi et al. |
| 5,951,546 A | 9/1999 | Lorentzen | 6,221,039 B1 | 4/2001 | Durgin et al. |
| 5,951,549 A | 9/1999 | Richardson et al. | 6,223,100 B1 | 4/2001 | Green |
| 5,954,720 A | 9/1999 | Wilson et al. | 6,224,593 B1 | 5/2001 | Ryan et al. |
| 5,954,731 A | 9/1999 | Yoon | 6,224,614 B1 | 5/2001 | Yoon |
| 5,954,733 A | 9/1999 | Yoon | 6,228,080 B1 | 5/2001 | Gines |
| 5,957,923 A | 9/1999 | Hahnen et al. | 6,228,083 B1 | 5/2001 | Lands et al. |
| 5,957,937 A | 9/1999 | Yoon | 6,248,124 B1 | 6/2001 | Pedros et al. |
| 5,960,544 A | 10/1999 | Beyers | 6,248,944 B1 | 6/2001 | Ito |
| 5,961,514 A | 10/1999 | Long et al. | 6,261,307 B1 | 7/2001 | Yoon et al. |
| 5,964,758 A | 10/1999 | Dresden | 6,267,761 B1 | 7/2001 | Ryan |
| 5,976,132 A | 11/1999 | Morris | 6,270,497 B1 | 8/2001 | Sekino et al. |
| 5,984,932 A | 11/1999 | Yoon | 6,270,508 B1 | 8/2001 | Klieman et al. |
| 5,984,938 A | 11/1999 | Yoon | 6,273,887 B1 | 8/2001 | Yamauchi et al. |
| 5,984,939 A | 11/1999 | Yoon | 6,277,117 B1 | 8/2001 | Tetzlaff et al. |
| 5,989,277 A | 11/1999 | LeMaire, III et al. | 6,280,458 B1 | 8/2001 | Boche et al. |
| 5,993,466 A | 11/1999 | Yoon | 6,283,961 B1 | 9/2001 | Underwood et al. |
| 5,993,467 A | 11/1999 | Yoon | D449,886 S | 10/2001 | Tetzlaff et al. |
| 5,997,565 A | 12/1999 | Inoue | 6,298,550 B1 | 10/2001 | Kirwan |
| 6,004,332 A | 12/1999 | Yoon et al. | 6,302,424 B1 | 10/2001 | Gisinger et al. |
| 6,004,335 A | 12/1999 | Vaitekunas et al. | 6,319,262 B1 | 11/2001 | Bates et al. |
| 6,010,516 A | 1/2000 | Hulka et al. | 6,319,451 B1 | 11/2001 | Brune |
| 6,017,358 A | 1/2000 | Yoon et al. | 6,322,561 B1 | 11/2001 | Eggers et al. |
| 6,021,693 A | 2/2000 | Feng-Sing | 6,322,580 B1 | 11/2001 | Kanner |
| 6,024,741 A | 2/2000 | Williamson et al. | 6,325,795 B1 | 12/2001 | Lindemann et al. |
| 6,024,743 A | 2/2000 | Edwards | 6,334,860 B1 | 1/2002 | Dorn |
| 6,024,744 A | 2/2000 | Kese et al. | 6,334,861 B1 | 1/2002 | Chandler et al. |
| 6,027,522 A | 2/2000 | Palmer | 6,345,532 B1 | 2/2002 | Coudray et al. |
| 6,030,384 A | 2/2000 | Nezhat | 6,350,264 B1 | 2/2002 | Hooven |
| 6,033,399 A | 3/2000 | Gines | 6,352,536 B1 | 3/2002 | Buysse et al. |
| 6,039,733 A | 3/2000 | Buysse et al. | 6,358,249 B1 | 3/2002 | Chen et al. |
| 6,041,679 A | 3/2000 | Slater et al. | 6,358,259 B1 | 3/2002 | Swain et al. |
| 6,050,996 A | 4/2000 | Schmaltz et al. | 6,358,268 B1 | 3/2002 | Hunt et al. |
| 6,053,914 A | 4/2000 | Eggers et al. | 6,364,879 B1 | 4/2002 | Chen et al. |
| 6,053,933 A | 4/2000 | Balazs et al. | D457,958 S | 5/2002 | Dycus et al. |
| D424,694 S | 5/2000 | Tetzlaff et al. | D457,959 S | 5/2002 | Tetzlaff et al. |
| D425,201 S | 5/2000 | Tetzlaff et al. | 6,387,094 B1 | 5/2002 | Eitenmuller |

| | | | |
|---|---|---|---|
| 6,391,035 B1 | 5/2002 | Appleby et al. | |
| 6,398,779 B1 | 6/2002 | Buysse et al. | |
| 6,402,747 B1 | 6/2002 | Lindemann et al. | |
| 6,409,728 B1 | 6/2002 | Ehr et al. | |
| H2037 H | 7/2002 | Yates et al. | |
| 6,419,675 B1 | 7/2002 | Gallo, Sr. | |
| 6,425,896 B1 | 7/2002 | Baltschun et al. | |
| 6,432,112 B2 | 8/2002 | Brock et al. | |
| 6,440,144 B1 | 8/2002 | Bacher | |
| 6,443,952 B1 | 9/2002 | Mulier et al. | |
| 6,443,970 B1 | 9/2002 | Schulze et al. | |
| 6,451,018 B1 | 9/2002 | Lands et al. | |
| 6,458,125 B1 | 10/2002 | Cosmescu | |
| 6,458,128 B1 | 10/2002 | Schulze | |
| 6,458,130 B1 | 10/2002 | Frazier et al. | |
| 6,461,352 B2 | 10/2002 | Morgan et al. | |
| 6,461,368 B2 | 10/2002 | Fogarty et al. | |
| 6,464,701 B1 | 10/2002 | Hooven et al. | |
| 6,464,702 B2 | 10/2002 | Schulze et al. | |
| 6,464,704 B2 | 10/2002 | Schmaltz et al. | |
| 6,485,489 B2 | 11/2002 | Teirstein et al. | |
| 6,494,888 B1 | 12/2002 | Laufer et al. | |
| 6,500,176 B1 | 12/2002 | Truckai et al. | |
| 6,506,196 B1 | 1/2003 | Laufer | |
| 6,508,815 B1 | 1/2003 | Strul et al. | |
| 6,511,480 B1 | 1/2003 | Tetzlaff et al. | |
| 6,514,215 B1 | 2/2003 | Ouchi | |
| 6,514,252 B2 | 2/2003 | Nezhat et al. | |
| 6,517,539 B1 | 2/2003 | Smith et al. | |
| 6,527,771 B1 | 3/2003 | Weadock et al. | |
| 6,533,784 B2 | 3/2003 | Truckai et al. | |
| 6,545,239 B2 | 4/2003 | Spedale et al. | |
| 6,558,385 B1 | 5/2003 | McClurken et al. | |
| 6,562,037 B2 | 5/2003 | Paton et al. | |
| 6,569,105 B1 | 5/2003 | Kortenbach et al. | |
| 6,582,450 B2 | 6/2003 | Ouchi | |
| 6,585,735 B1 | 7/2003 | Frazier et al. | |
| 6,602,252 B2 | 8/2003 | Mollenauer | |
| 6,605,790 B2 | 8/2003 | Yoshida | |
| 6,616,658 B2 | 9/2003 | Ineson | |
| 6,616,661 B2 | 9/2003 | Wellman et al. | |
| 6,620,161 B2 | 9/2003 | Schulze et al. | |
| 6,620,184 B2 | 9/2003 | De Laforcade et al. | |
| 6,626,901 B1 | 9/2003 | Treat et al. | |
| 6,638,287 B2 | 10/2003 | Danitz et al. | |
| 6,641,595 B1 | 11/2003 | Moran et al. | |
| 6,652,514 B2 | 11/2003 | Ellman et al. | |
| 6,652,521 B2 | 11/2003 | Schulze | |
| 6,656,175 B2 | 12/2003 | Francischelli et al. | |
| 6,656,177 B2 | 12/2003 | Truckai et al. | |
| 6,660,072 B2 | 12/2003 | Chatterjee | |
| 6,663,639 B1 | 12/2003 | Laufer et al. | |
| 6,663,641 B1 | 12/2003 | Kovac et al. | |
| 6,666,854 B1 | 12/2003 | Lange | |
| 6,669,696 B2 | 12/2003 | Bacher et al. | |
| 6,673,092 B1 | 1/2004 | Bacher | |
| 6,676,660 B2 | 1/2004 | Wampler et al. | |
| 6,676,676 B2 | 1/2004 | Danitz et al. | |
| 6,679,882 B1 | 1/2004 | Kornerup | |
| 6,682,527 B2 | 1/2004 | Strul | |
| 6,682,528 B2 | 1/2004 | Frazier et al. | |
| 6,685,724 B1 | 2/2004 | Haluck | |
| 6,689,131 B2 | 2/2004 | McClurken | |
| 6,692,445 B2 | 2/2004 | Roberts et al. | |
| 6,693,246 B1 | 2/2004 | Rudolph et al. | |
| 6,695,840 B2 | 2/2004 | Schulze | |
| 6,702,810 B2 | 3/2004 | McClurken et al. | |
| 6,723,092 B2 | 4/2004 | Brown et al. | |
| 6,726,068 B2 | 4/2004 | Miller | |
| 6,726,686 B2 | 4/2004 | Buysse et al. | |
| 6,726,694 B2 | 4/2004 | Blatter et al. | |
| 6,733,498 B2 | 5/2004 | Paton et al. | |
| 6,736,813 B2 | 5/2004 | Yamauchi et al. | |
| 6,743,229 B2 | 6/2004 | Buysse et al. | |
| 6,743,230 B2 | 6/2004 | Lutze et al. | |
| 6,743,239 B1 | 6/2004 | Kuehn et al. | |
| 6,743,240 B2 | 6/2004 | Smith et al. | |
| 6,755,843 B2 | 6/2004 | Chung et al. | |
| 6,756,553 B1 | 6/2004 | Yamaguchi et al. | |
| 6,757,977 B2 | 7/2004 | Dambal et al. | |
| D493,888 S | 8/2004 | Reschke | |
| 6,770,072 B1 | 8/2004 | Truckai et al. | |
| 6,773,409 B2 | 8/2004 | Truckai et al. | |
| 6,773,432 B1 | 8/2004 | Clayman et al. | |
| 6,773,434 B2 | 8/2004 | Ciarrocca | |
| 6,773,441 B1 | 8/2004 | Laufer et al. | |
| 6,775,575 B2 | 8/2004 | Bommannan et al. | |
| 6,776,780 B2 | 8/2004 | Mulier et al. | |
| 6,786,905 B2 | 9/2004 | Swanson et al. | |
| 6,790,217 B2 | 9/2004 | Schulze et al. | |
| 6,796,981 B2 | 9/2004 | Wham et al. | |
| D496,997 S | 10/2004 | Dycus et al. | |
| 6,800,825 B1 | 10/2004 | Sasaki et al. | |
| 6,802,843 B2 | 10/2004 | Truckai et al. | |
| 6,808,525 B2 | 10/2004 | Latterell et al. | |
| D499,181 S | 11/2004 | Dycus et al. | |
| 6,818,000 B2 | 11/2004 | Muller et al. | |
| 6,821,285 B2 | 11/2004 | Laufer et al. | |
| 6,835,200 B2 | 12/2004 | Laufer et al. | |
| 6,857,357 B2 | 2/2005 | Fujii | |
| 6,860,880 B2 | 3/2005 | Treat et al. | |
| 6,887,240 B1 | 5/2005 | Lands et al. | |
| 6,889,116 B2 | 5/2005 | Jinno | |
| 6,914,201 B2 | 7/2005 | Van Vooren et al. | |
| 6,926,716 B2 | 8/2005 | Baker et al. | |
| 6,929,644 B2 | 8/2005 | Truckai et al. | |
| 6,932,810 B2 | 8/2005 | Ryan | |
| 6,932,816 B2 | 8/2005 | Phan | |
| 6,934,134 B2 | 8/2005 | Mori et al. | |
| 6,936,061 B2 | 8/2005 | Sasaki | |
| D509,297 S | 9/2005 | Wells | |
| 6,942,662 B2 | 9/2005 | Goble et al. | |
| 6,943,311 B2 | 9/2005 | Miyako | |
| 6,953,430 B2 | 10/2005 | Kidooka | |
| 6,953,461 B2 | 10/2005 | McClurken et al. | |
| 6,958,070 B2 | 10/2005 | Witt et al. | |
| 6,960,210 B2 | 11/2005 | Lands et al. | |
| 6,964,662 B2 | 11/2005 | Kidooka | |
| 6,966,907 B2 | 11/2005 | Goble | |
| 6,972,017 B2 | 12/2005 | Smith et al. | |
| 6,977,495 B2 | 12/2005 | Donofrio | |
| 6,979,786 B2 | 12/2005 | Aukland et al. | |
| 6,981,628 B2 | 1/2006 | Wales | |
| 6,987,244 B2 | 1/2006 | Bauer | |
| 6,994,707 B2 | 2/2006 | Ellman et al. | |
| 6,994,709 B2 | 2/2006 | Iida | |
| 6,997,931 B2 | 2/2006 | Sauer et al. | |
| 7,001,381 B2 | 2/2006 | Harano et al. | |
| 7,011,657 B2 | 3/2006 | Truckai et al. | |
| 7,033,354 B2 | 4/2006 | Keppel | |
| 7,033,356 B2 | 4/2006 | Latterell et al. | |
| 7,041,102 B2 | 5/2006 | Truckai et al. | |
| 7,044,948 B2 | 5/2006 | Keppel | |
| 7,052,489 B2 | 5/2006 | Griego et al. | |
| 7,052,496 B2 | 5/2006 | Yamauchi | |
| 7,063,715 B2 | 6/2006 | Onuki et al. | |
| D525,361 S | 7/2006 | Hushka | |
| 7,070,597 B2 | 7/2006 | Truckai et al. | |
| 7,083,618 B2 | 8/2006 | Couture et al. | |
| 7,083,619 B2 | 8/2006 | Truckai et al. | |
| 7,083,620 B2 | 8/2006 | Jahns et al. | |
| 7,087,051 B2 | 8/2006 | Bourne et al. | |
| 7,087,054 B2 | 8/2006 | Truckai et al. | |
| 7,090,673 B2 | 8/2006 | Dycus et al. | |
| 7,090,689 B2 | 8/2006 | Nagase et al. | |
| 7,101,371 B2 | 9/2006 | Dycus et al. | |
| 7,101,372 B2 | 9/2006 | Dycus et al. | |
| 7,101,373 B2 | 9/2006 | Dycus et al. | |
| 7,103,947 B2 | 9/2006 | Sartor et al. | |
| 7,107,124 B2 | 9/2006 | Green | |
| 7,112,199 B2 | 9/2006 | Cosmescu | |
| D531,311 S | 10/2006 | Guerra et al. | |
| 7,115,123 B2 | 10/2006 | Knowlton et al. | |
| 7,118,570 B2 | 10/2006 | Tetzlaff et al. | |
| 7,118,587 B2 | 10/2006 | Dycus et al. | |
| 7,131,860 B2 | 11/2006 | Sartor et al. | |
| 7,131,970 B2 | 11/2006 | Moses et al. | |
| 7,131,971 B2 | 11/2006 | Dycus et al. | |

| Patent No. | Date | Inventor |
|---|---|---|
| 7,135,020 B2 | 11/2006 | Lawes et al. |
| D533,942 S | 12/2006 | Kerr et al. |
| 7,145,757 B2 | 12/2006 | Shea et al. |
| 7,147,638 B2 | 12/2006 | Chapman et al. |
| 7,150,097 B2 | 12/2006 | Sremcich et al. |
| 7,150,749 B2 | 12/2006 | Dycus et al. |
| 7,153,314 B2 | 12/2006 | Laufer et al. |
| D535,027 S | 1/2007 | James et al. |
| 7,156,842 B2 | 1/2007 | Sartor et al. |
| 7,156,846 B2 | 1/2007 | Dycus et al. |
| 7,160,298 B2 | 1/2007 | Lawes et al. |
| 7,160,299 B2 | 1/2007 | Baily |
| 7,169,146 B2 | 1/2007 | Truckai et al. |
| 7,179,255 B2 | 2/2007 | Lettice et al. |
| 7,179,258 B2 | 2/2007 | Buysse et al. |
| 7,195,631 B2 | 3/2007 | Dumbauld |
| D541,418 S | 4/2007 | Schechter et al. |
| 7,207,990 B2 | 4/2007 | Lands et al. |
| D541,938 S | 5/2007 | Kerr et al |
| 7,223,264 B2 | 5/2007 | Daniel et al. |
| 7,223,265 B2 | 5/2007 | Keppel |
| 7,232,440 B2 | 6/2007 | Dumbauld et al. |
| 7,241,288 B2 | 7/2007 | Braun |
| 7,241,296 B2 | 7/2007 | Buysse et al. |
| 7,244,257 B2 | 7/2007 | Podjahsky et al. |
| 7,246,734 B2 | 7/2007 | Shelto, IV |
| 7,248,944 B2 | 7/2007 | Green |
| 7,252,667 B2 | 8/2007 | Moses et al. |
| 7,255,697 B2 | 8/2007 | Dycus et al. |
| 7,267,677 B2 | 9/2007 | Johnson et al. |
| 7,270,660 B2 | 9/2007 | Ryan |
| 7,270,664 B2 | 9/2007 | Johnson et al. |
| 7,276,068 B2 | 10/2007 | Johnson et al. |
| 7,300,435 B2 | 11/2007 | Wham et al. |
| 7,303,557 B2 | 12/2007 | Wham et al. |
| 7,311,709 B2 | 12/2007 | Truckai et al. |
| 7,314,471 B2 | 1/2008 | Holman |
| 7,318,823 B2 | 1/2008 | Sharps et al. |
| 7,329,256 B2 | 2/2008 | Johnson et al. |
| 7,329,257 B2 | 2/2008 | Kanehira et al. |
| D564,662 S | 3/2008 | Moses et al. |
| 7,338,526 B2 | 3/2008 | Steinberg |
| 7,342,754 B2 | 3/2008 | Fitzgerald et al. |
| 7,344,268 B2 | 3/2008 | Jhigamian |
| D567,943 S | 4/2008 | Moses et al. |
| 7,367,976 B2 | 5/2008 | Lawes et al. |
| 7,377,920 B2 | 5/2008 | Buysse et al. |
| 7,384,420 B2 | 6/2008 | Dycus et al. |
| 7,384,421 B2 | 6/2008 | Hushka |
| 7,396,336 B2 | 7/2008 | Orszulak et al. |
| D575,395 S | 8/2008 | Hushka |
| D575,401 S | 8/2008 | Hixson et al. |
| 7,435,249 B2 | 10/2008 | Buysse et al. |
| 7,442,193 B2 | 10/2008 | Shields et al. |
| 7,442,194 B2 | 10/2008 | Dumbauld et al. |
| 7,445,621 B2 | 11/2008 | Dumbauld et al. |
| 7,458,972 B2 | 12/2008 | Keppel |
| 7,473,253 B2 | 1/2009 | Dycus et al. |
| 7,481,810 B2 | 1/2009 | Dumbauld et al. |
| 7,487,780 B2 | 2/2009 | Hooven |
| 7,491,201 B2 | 2/2009 | Shields et al. |
| 7,491,202 B2 | 2/2009 | Odom et al. |
| 7,500,975 B2 | 3/2009 | Cunningham et al. |
| 7,510,556 B2 | 3/2009 | Nguyen et al. |
| 7,513,898 B2 | 4/2009 | Johnson et al. |
| 7,540,872 B2 | 6/2009 | Schechter et al. |
| 7,549,995 B2 | 6/2009 | Schultz |
| 7,553,312 B2 | 6/2009 | Tetzlaff et al. |
| 2002/0013583 A1 | 1/2002 | Camran et al. |
| 2002/0049442 A1 | 4/2002 | Roberts et al. |
| 2002/0099372 A1 | 7/2002 | Schulze et al. |
| 2002/0107517 A1 | 8/2002 | Witt et al. |
| 2002/0111624 A1 | 8/2002 | Witt et al. |
| 2002/0188294 A1 | 12/2002 | Couture et al. |
| 2003/0014052 A1 | 1/2003 | Buysse et al. |
| 2003/0014053 A1 | 1/2003 | Nguyen et al. |
| 2003/0018331 A1 | 1/2003 | Dycus et al. |
| 2003/0018332 A1 | 1/2003 | Schmaltz et al. |
| 2003/0032956 A1 | 2/2003 | Lands et al. |
| 2003/0069570 A1 | 4/2003 | Witzel et al. |
| 2003/0069571 A1 | 4/2003 | Treat et al. |
| 2003/0078578 A1 | 4/2003 | Truckai et al. |
| 2003/0109875 A1 | 6/2003 | Tetzlaff et al. |
| 2003/0114851 A1 | 6/2003 | Truckai et al. |
| 2003/0139741 A1 | 7/2003 | Goble et al. |
| 2003/0139742 A1 | 7/2003 | Wampler et al. |
| 2003/0158548 A1 | 8/2003 | Phan et al. |
| 2003/0158549 A1 | 8/2003 | Swanson |
| 2003/0171747 A1 | 9/2003 | Kanehira et al. |
| 2003/0181910 A1 | 9/2003 | Dycus et al. |
| 2003/0216732 A1 | 11/2003 | Truckai et al. |
| 2003/0220637 A1 | 11/2003 | Truckai et al. |
| 2003/0229344 A1 | 12/2003 | Dycus et al. |
| 2003/0236325 A1 | 12/2003 | Bonora |
| 2003/0236518 A1 | 12/2003 | Marchitto et al. |
| 2004/0030330 A1 | 2/2004 | Brassell et al. |
| 2004/0030332 A1 | 2/2004 | Knowlton et al. |
| 2004/0049185 A1 | 3/2004 | Latterell et al. |
| 2004/0064151 A1 | 4/2004 | Mollenauer |
| 2004/0073238 A1 | 4/2004 | Makower |
| 2004/0073256 A1 | 4/2004 | Marchitto et al. |
| 2004/0078035 A1 | 4/2004 | Kanehira et al. |
| 2004/0082952 A1 | 4/2004 | Dycus et al. |
| 2004/0087943 A1 | 5/2004 | Dycus et al. |
| 2004/0115296 A1 | 6/2004 | Duffin |
| 2004/0116924 A1 | 6/2004 | Dycus et al. |
| 2004/0116979 A1 | 6/2004 | Truckai et al. |
| 2004/0143263 A1 | 7/2004 | Schechter et al. |
| 2004/0148035 A1 | 7/2004 | Barrett et al. |
| 2004/0162557 A1 | 8/2004 | Tetzlaff et al. |
| 2004/0193153 A1 | 9/2004 | Sarter et al. |
| 2004/0199181 A1 | 10/2004 | Knodel et al. |
| 2004/0210282 A1 | 10/2004 | Flock et al. |
| 2004/0224590 A1 | 11/2004 | Rawa et al. |
| 2004/0230189 A1 | 11/2004 | Keppel |
| 2004/0236326 A1 | 11/2004 | Schulze et al. |
| 2004/0243125 A1 | 12/2004 | Dycus et al. |
| 2004/0249374 A1 | 12/2004 | Tetzlaff et al. |
| 2004/0260281 A1 | 12/2004 | Baxter, III et al. |
| 2005/0004564 A1 | 1/2005 | Wham et al. |
| 2005/0004569 A1 | 1/2005 | Witt et al. |
| 2005/0033278 A1 | 2/2005 | McClurken et al. |
| 2005/0059934 A1 | 3/2005 | Wenchell et al. |
| 2005/0096645 A1 | 5/2005 | Wellman et al. |
| 2005/0101951 A1 | 5/2005 | Wham et al. |
| 2005/0101952 A1 | 5/2005 | Lands et al. |
| 2005/0113818 A1 | 5/2005 | Sartor et al. |
| 2005/0113819 A1 | 5/2005 | Wham et al. |
| 2005/0113826 A1 | 5/2005 | Johnson et al. |
| 2005/0149017 A1 | 7/2005 | Dycus |
| 2005/0149151 A1 | 7/2005 | Orszulak et al. |
| 2005/0154387 A1 | 7/2005 | Moses et al. |
| 2005/0187547 A1 | 8/2005 | Sugi |
| 2005/0197659 A1 | 9/2005 | Bahney |
| 2005/0203504 A1 | 9/2005 | Wham et al. |
| 2006/0052778 A1 | 3/2006 | Chapman et al. |
| 2006/0052779 A1 | 3/2006 | Hammill |
| 2006/0064085 A1 | 3/2006 | Schechter et al. |
| 2006/0064086 A1 | 3/2006 | Odom |
| 2006/0074417 A1 | 4/2006 | Cunningham et al. |
| 2006/0079888 A1 | 4/2006 | Mulier et al. |
| 2006/0079890 A1 | 4/2006 | Guerra |
| 2006/0079891 A1 | 4/2006 | Arts et al. |
| 2006/0079933 A1 | 4/2006 | Hushka et al. |
| 2006/0084973 A1 | 4/2006 | Hushka |
| 2006/0089670 A1 | 4/2006 | Hushka |
| 2006/0116675 A1 | 6/2006 | McClurken et al. |
| 2006/0129146 A1 | 6/2006 | Dycus et al. |
| 2006/0167450 A1 | 7/2006 | Johnson et al. |
| 2006/0167452 A1 | 7/2006 | Moses et al. |
| 2006/0173452 A1 | 8/2006 | Buysse et al. |
| 2006/0189981 A1 | 8/2006 | Dycus et al. |
| 2006/0190035 A1 | 8/2006 | Hushka et al. |
| 2006/0217709 A1 | 9/2006 | Couture et al. |
| 2006/0229666 A1 | 10/2006 | Suzuki et al. |
| 2006/0253126 A1 | 11/2006 | Bjerken et al. |
| 2006/0259036 A1 | 11/2006 | Tetzlaff et al. |
| 2006/0264922 A1 | 11/2006 | Sartor et al. |

| | | |
|---|---|---|
| 2006/0264931 A1 | 11/2006 | Chapman et al. |
| 2006/0283093 A1 | 12/2006 | Petrovic et al. |
| 2006/0287641 A1 | 12/2006 | Perlin |
| 2007/0016182 A1 | 1/2007 | Lipson et al. |
| 2007/0016187 A1 | 1/2007 | Weinberg et al. |
| 2007/0043352 A1 | 2/2007 | Garrison et al. |
| 2007/0043353 A1 | 2/2007 | Dycus et al. |
| 2007/0060919 A1 | 3/2007 | Isaacson et al. |
| 2007/0062017 A1 | 3/2007 | Dycus et al. |
| 2007/0074807 A1 | 4/2007 | Guerra |
| 2007/0078456 A1 | 4/2007 | Dumbauld et al. |
| 2007/0078458 A1 | 4/2007 | Dumbauld et al. |
| 2007/0078459 A1 | 4/2007 | Johnson et al. |
| 2007/0088356 A1 | 4/2007 | Moses et al. |
| 2007/0106295 A1 | 5/2007 | Garrison et al. |
| 2007/0106297 A1 | 5/2007 | Dumbauld et al. |
| 2007/0118111 A1 | 5/2007 | Weinberg |
| 2007/0118115 A1 | 5/2007 | Artale et al. |
| 2007/0142833 A1 | 6/2007 | Dycus et al. |
| 2007/0142834 A1 | 6/2007 | Dumbauld |
| 2007/0156139 A1 | 7/2007 | Schechter et al. |
| 2007/0156140 A1 | 7/2007 | Baily |
| 2007/0173811 A1 | 7/2007 | Couture et al. |
| 2007/0173814 A1 | 7/2007 | Hixson et al. |
| 2007/0179499 A1 | 8/2007 | Garrison |
| 2007/0198011 A1 | 8/2007 | Sugita |
| 2007/0213712 A1 | 9/2007 | Buysse et al. |
| 2007/0255279 A1 | 11/2007 | Buysse et al. |
| 2007/0260235 A1 | 11/2007 | Podhajsky |
| 2007/0260238 A1 | 11/2007 | Guerra |
| 2007/0260241 A1 | 11/2007 | Dalla Betta et al. |
| 2007/0260242 A1 | 11/2007 | Dycus et al. |
| 2007/0265616 A1 | 11/2007 | Couture et al. |
| 2008/0004616 A1 | 1/2008 | Patrick |
| 2008/0009860 A1 | 1/2008 | Odom |
| 2008/0015575 A1 | 1/2008 | Odom et al. |
| 2008/0021450 A1 | 1/2008 | Couture |
| 2008/0033428 A1 | 2/2008 | Artale et al. |
| 2008/0039835 A1 | 2/2008 | Johnson et al. |
| 2008/0039836 A1 | 2/2008 | Odom et al. |
| 2008/0045947 A1 | 2/2008 | Johnson et al. |
| 2008/0058802 A1 | 3/2008 | Couture et al. |
| 2008/0082100 A1 | 4/2008 | Orton et al. |
| 2008/0091189 A1 | 4/2008 | Carlton |
| 2008/0114356 A1 | 5/2008 | Johnson et al. |
| 2008/0167651 A1 | 7/2008 | Tetzlaff et al. |
| 2008/0195093 A1 | 8/2008 | Couture et al. |
| 2008/0215051 A1 | 9/2008 | Buysse et al. |
| 2008/0243120 A1 | 10/2008 | Lawes et al. |
| 2008/0249527 A1 | 10/2008 | Couture |
| 2008/0312653 A1 | 12/2008 | Arts et al. |
| 2008/0319442 A1 | 12/2008 | Unger et al. |
| 2009/0012520 A1 | 1/2009 | Hixson et al. |
| 2009/0018535 A1 | 1/2009 | Schechter et al. |
| 2009/0024126 A1 | 1/2009 | Artale et al. |
| 2009/0043304 A1 | 2/2009 | Tetzlaff et al. |
| 2009/0048596 A1 | 2/2009 | Shields et al. |
| 2009/0062794 A1 | 3/2009 | Buysse et al. |
| 2009/0082766 A1 | 3/2009 | Unger et al. |
| 2009/0082767 A1 | 3/2009 | Unger et al. |
| 2009/0082769 A1 | 3/2009 | Unger et al. |
| 2009/0088738 A1 | 4/2009 | Guerra et al. |
| 2009/0088739 A1 | 4/2009 | Hushka et al. |
| 2009/0088740 A1 | 4/2009 | Guerra et al. |
| 2009/0088741 A1 | 4/2009 | Hushka et al. |
| 2009/0088744 A1 | 4/2009 | Townsend |
| 2009/0088745 A1 | 4/2009 | Hushka et al. |
| 2009/0088746 A1 | 4/2009 | Hushka et al. |
| 2009/0088747 A1 | 4/2009 | Hushka et al. |
| 2009/0088748 A1 | 4/2009 | Guerra et al. |
| 2009/0088749 A1 | 4/2009 | Hushka et al. |
| 2009/0088750 A1 | 4/2009 | Hushka et al. |
| 2009/0112206 A1 | 4/2009 | Dumbauld et al. |
| 2009/0131934 A1 | 5/2009 | Odom et al. |
| 2009/0149853 A1 | 6/2009 | Shields et al. |
| 2009/0149854 A1 | 6/2009 | Cunningham et al. |
| 2009/0171350 A1 | 7/2009 | Dycus et al. |
| 2009/0171353 A1 | 7/2009 | Johnson et al. |
| 2009/0182327 A1 | 7/2009 | Unger |
| 2009/0187188 A1 | 7/2009 | Guerra et al. |

FOREIGN PATENT DOCUMENTS

| | | |
|---|---|---|
| DE | 2415263 | 10/1975 |
| DE | 2514501 | 10/1976 |
| DE | 2627679 | 1/1977 |
| DE | 3612646 | 4/1987 |
| DE | 8712328 | 3/1988 |
| DE | 4303882 | 8/1994 |
| DE | 4403252 | 8/1995 |
| DE | 19515914 | 7/1996 |
| DE | 29616210 | 1/1997 |
| DE | 19608716 | 4/1997 |
| DE | 19751106 | 5/1998 |
| DE | 19751108 | 5/1999 |
| DE | 19738457 | 1/2009 |
| EP | 0364216 | 4/1990 |
| EP | 0467501 | 1/1992 |
| EP | 0518230 | 12/1992 |
| EP | 0541930 | 5/1993 |
| EP | 0572131 | 12/1993 |
| EP | 0584787 | 3/1994 |
| EP | 0589453 | 3/1994 |
| EP | 0589555 | 3/1994 |
| EP | 0623316 | 11/1994 |
| EP | 0624348 | 11/1994 |
| EP | 0650701 | 5/1995 |
| EP | 0694290 | 3/1996 |
| EP | 0717966 | 6/1996 |
| EP | 0754437 | 3/1997 |
| EP | 0517243 | 9/1997 |
| EP | 0853922 | 7/1998 |
| EP | 0875209 | 11/1998 |
| EP | 0878169 | 11/1998 |
| EP | 0887046 | 1/1999 |
| EP | 0923907 | 6/1999 |
| EP | 0986990 | 3/2000 |
| EP | 1034747 | 9/2000 |
| EP | 1034748 | 9/2000 |
| EP | 1025807 | 10/2000 |
| EP | 1034746 | 10/2000 |
| EP | 1050278 | 11/2000 |
| EP | 1053719 | 11/2000 |
| EP | 1053720 | 11/2000 |
| EP | 1055399 | 11/2000 |
| EP | 1055400 | 11/2000 |
| EP | 1080694 | 3/2001 |
| EP | 1082944 | 3/2001 |
| EP | 1159926 | 12/2001 |
| EP | 1177771 | 2/2002 |
| EP | 1301135 | 4/2003 |
| EP | 1330991 | 7/2003 |
| EP | 1486177 | 6/2004 |
| EP | 1472984 | 11/2004 |
| EP | 0774232 | 1/2005 |
| EP | 1527747 | 5/2005 |
| EP | 1530952 | 5/2005 |
| EP | 1532932 | 5/2005 |
| EP | 1535581 | 6/2005 |
| EP | 1609430 | 12/2005 |
| EP | 1632192 | 3/2006 |
| EP | 1642543 | 4/2006 |
| EP | 1645238 | 4/2006 |
| EP | 1645240 | 4/2006 |
| EP | 1649821 | 4/2006 |
| EP | 1707143 | 10/2006 |
| EP | 1769765 | 4/2007 |
| EP | 1769766 | 4/2007 |
| EP | 1929970 | 6/2008 |
| EP | 1683496 | 12/2008 |
| GB | 623316 | 5/1949 |
| GB | 1490585 | 11/1977 |
| GB | 2214430 A | 6/1989 |
| GB | 2213416 A | 8/1989 |
| JP | 61-501068 | 9/1984 |
| JP | 65-502328 | 3/1992 |
| JP | 5-5106 | 1/1993 |

| | | |
|---|---|---|
| JP | 5-40112 | 2/1993 |
| JP | 06343644 A2 | 12/1994 |
| JP | 07265328 A2 | 10/1995 |
| JP | 08056955 A2 | 3/1996 |
| JP | 08252263 A2 | 10/1996 |
| JP | 09010223 A2 | 1/1997 |
| JP | 11244298 A2 | 9/1999 |
| JP | 2000-342599 A2 | 12/2000 |
| JP | 2000-350732 A2 | 12/2000 |
| JP | 2001-008944 A2 | 1/2001 |
| JP | 2001-029356 A2 | 2/2001 |
| JP | 2001-128990 A2 | 5/2001 |
| SU | 401367 | 11/1974 |
| WO | WO 89/00757 | 1/1989 |
| WO | WO 92/04873 | 4/1992 |
| WO | WO 92/06642 | 4/1992 |
| WO | WO 93/21845 | 11/1993 |
| WO | WO 94/08524 | 4/1994 |
| WO | WO 94/20025 | 9/1994 |
| WO | WO 95/02369 | 1/1995 |
| WO | WO 95/07662 | 3/1995 |
| WO | WO 95/15124 | 6/1995 |
| WO | WO 96/05776 | 2/1996 |
| WO | WO 96/22056 | 7/1996 |
| WO | WO 96/13218 | 9/1996 |
| WO | WO 97/00646 | 1/1997 |
| WO | WO 97/00647 | 1/1997 |
| WO | WO 97/10764 | 3/1997 |
| WO | WO 97/24073 | 7/1997 |
| WO | WO 97/24993 | 7/1997 |
| WO | WO 98/27880 | 7/1998 |
| WO | WO 99/03407 | 1/1999 |
| WO | WO 99/03408 | 1/1999 |
| WO | WO 99/03409 | 1/1999 |
| WO | WO 99/12488 | 3/1999 |
| WO | WO 99/23933 | 5/1999 |
| WO | WO 99/40857 | 8/1999 |
| WO | WO 99/40861 | 8/1999 |
| WO | WO 99/51158 | 10/1999 |
| WO | WO 99/66850 | 12/1999 |
| WO | WO 00/24330 | 5/2000 |
| WO | WO 00/24331 | 5/2000 |
| WO | WO 00/36986 | 6/2000 |
| WO | WO 00/41638 | 7/2000 |
| WO | WO 00/47124 | 8/2000 |
| WO | WO 00/53112 | 9/2000 |
| WO | WO 01/17448 | 3/2001 |
| WO | WO 01/54604 | 8/2001 |
| WO | WO 02/07627 | 1/2002 |
| WO | WO 02/067798 | 9/2002 |
| WO | WO 02/080783 | 10/2002 |
| WO | WO 02/080784 | 10/2002 |
| WO | WO 02/080785 | 10/2002 |
| WO | WO 02/080786 | 10/2002 |
| WO | WO 02/080793 | 10/2002 |
| WO | WO 02/080794 | 10/2002 |
| WO | WO 02/080795 | 10/2002 |
| WO | WO 02/080796 | 10/2002 |
| WO | WO 02/080797 | 10/2002 |
| WO | WO 02/080798 | 10/2002 |
| WO | WO 02/080799 | 10/2002 |
| WO | WO 02/081170 | 10/2002 |
| WO | WO 03/061500 | 7/2003 |
| WO | WO 03/090630 | 11/2003 |
| WO | WO 03/101311 | 12/2003 |
| WO | WO 2004/032776 | 4/2004 |
| WO | WO 2004/032777 | 4/2004 |
| WO | WO 2004/052221 | 6/2004 |
| WO | WO 2004/073488 | 9/2004 |
| WO | WO 2004/073490 | 9/2004 |
| WO | WO 2004/073753 | 9/2004 |
| WO | WO 2004/082495 | 9/2004 |
| WO | WO 2004/098383 | 11/2004 |
| WO | WO 2004/103156 | 12/2004 |
| WO | WO 2005/004734 | 1/2005 |
| WO | WO 2005/004735 | 1/2005 |
| WO | WO 2005/110264 | 11/2005 |
| WO | WO 2008/045348 | 4/2008 |
| WO | WO 2008/045350 | 4/2008 |

OTHER PUBLICATIONS

Chung et al., "Clinical Experience of Sutureless Closed Hemorrhoidectomy with LigaSure" Diseases of the Colon & Rectum vol. 46, No. 1 Jan. 2003.

Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.

Peterson et al. "Comparison of Healing Process Following Ligation with Sutures and Bipolar Vessel Sealing" Surgical Technology International (2001).

"Electrosurgery: A Historical Overview" Innovations in Electrosurgery; Sales/Product Literature; Dec. 31, 2000.

Johnson et al. "Evaluation of a Bipolar Electrothermal Vessel Sealing Device in Hemorrhoidectomy" Sales/Product Literature; Jan. 2004.

E. David Crawford "Evaluation of a New Vessel Sealing Device in Urologic Cancer Surgery" Sales/Product Literature 2000.

Johnson et al. "Evaluation of the LigaSure Vessel Sealing System in Hemorrhoidectormy" American College of Surgeons (ACS) Clinicla Congress Poster (2000).

Muller et al., "Extended Left Hemicolectomy Using the LigaSure Vessel Sealing System" Innovations That Work, Sep. 1999.

Kennedy et al. "High-burst-strength, feedback-controlled bipolar vessel sealing" Surgical Endoscopy (1998) 12: 876-878.

Carus et al., "Initial Experience With the LigaSure Vessel Sealing System in Abdominal Surgery" Innovations That Work, Jun. 2002.

Heniford et al. "Initial Research and Clinical Results with an Electrothermal Bipolar Vessel Sealer" Oct. 1999.

Heniford et al. "Initial Results with an Electrothermal Bipolar Vessel Sealer" Surgical Endoscopy (2000) 15:799-801.

Herman et al., "Laparoscopic Intestinal Resection With the LigaSure Vessel Sealing System: A Case Report"; Innovations That Work, Feb. 2002.

Koyle et al., "Laparoscopic Palomo Varicocele Ligation in Children and Adolescents" Pediatric Endosurgery & Innovative Techniques, vol. 6, No. 1, 2002.

W. Scott Helton, "LigaSure Vessel Sealing System: Revolutionary Hemostasis Product for General Surgery"; Sales/Product Literature 1999.

LigaSure Vessel Sealing System, the Seal of Confidence in General, Gynecologic, Urologic, and Laparoscopic Surgery; Sales/Product Literature; Apr. 2002.

Joseph Ortenberg "LigaSure System Used in Laparoscopic 1st and 2nd Stage Orchiopexy" Innovations That Work, Nov. 2002.

Sigel et al. "The Mechanism of Blood Vessel Closure by High Frequency Electrocoagulation" Surgery Gynecology & Obstetrics, Oct. 1965 pp. 823-831.

Sampayan et al, "Multilayer Ultra-High Gradient Insulator Technology" Discharges and Electrical Insulation in Vacuum, 1998. Netherlands Aug. 17-21, 1998; vol. 2, pp. 740-743.

Paul G. Horgan, "A Novel Technique for Parenchymal Division During Hepatectomy" The American Journal of Surgery, vol. 181, No. 3, Apr. 2001 pp. 236-237.

Olsson et al. "Radical Cystectomy in Females" Current Surgical Techniques in Urology, vol. 14, Issue 3, 2001.

Palazzo et al. "Randomized clinical trial of Ligasure versus open haemorrhoidectomy" British Journal of Surgery 2002, 89, 154-157.

Levy et al. "Randomized Trial of Suture Versus Electrosurgical Bipolar Vessel Sealing in Vaginal Hysterectomy" Obstetrics & Gynecology, vol. 102, No. 1, Jul. 2003.

"Reducing Needlestick Injuries in the Operating Room" Sales/Product Literature 2001.

Bergdahl et al. "Studies on Coagulation and the Development of an Automatic Computerized Bipolar Coagulator" J.Neurosurg, vol. 75, Jul. 1991, pp. 148-151.

Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.

Sayfan et al. "Sutureless Closed Hemorrhoidectomy: A New Technique" Annals of Surgery vol. 234 No. 1 Jul. 2001; pp. 21-24.

Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l. Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778 dated Oct. 31, 2000.
Int'l Search Report EP 98957771 dated Aug. 9, 2001.
Int'l Search Report EP 98958575.7 dated Sep. 20, 2002.
Int'l Search Report EP 04013772 dated Apr. 1, 2005.
Int'l Search Report EP 04027314 dated Mar. 10, 2005.
Int'l Search Report EP 04027479 dated Mar. 8, 2005.
Int'l Search Report EP 04027705 dated Feb. 3, 2005.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Sep. 28, 2005.
Int'l Search Report EP 05013895 dated Oct. 14, 2005.
Int'l Search Report EP 05016399 dated Jan. 5, 2006.
Int'l Search Report EP 05017281 dated Nov. 16, 2005.
Int'l Search Report EP 05019130.3 dated Oct. 18, 2005.
Int'l Search Report EP 05019429.9 dated May 6, 2008.
Int'l Search Report EP 05020665.5 dated Feb. 16, 2006.
Int'l Search Report EP 05020666.3 dated Feb. 17, 2006.
Int'l Search Report EP 05021197.8 dated Jan. 31, 2006.
Int'l Search Report EP 05021779.3 dated Jan. 18, 2006.
Int'l Search Report EP 05021780.1 dated Feb. 9, 2006.
Int'l Search Report EP 05021937.7 dated Jan. 13, 2006.
In'tl Search Report—extended—EP 05021937.7 dated Mar. 6, 2006.
Int'l Search Report EP 05023017.6 dated Feb. 16, 2006.
Int'l Search Report EP 06002279.5 dated Mar. 22, 2006.
Int'l Search Report EP 06005185.1 dated Apr. 18, 2006.
Int'l Search Report EP 06006716 dated Aug. 4, 2006.
Int'l Search Report EP 06008515.6 dated Jan. 8, 2009.
Int'l Search Report EP 06008779.8 dated Jun. 13, 2006.
Int'l Search Report EP 06014461.5 dated Oct. 20, 2006.
Int'l Search Report EP 06020574.7 dated Sep. 21, 2007.
Int'l Search Report EP 06020583.8 dated Jan. 30, 2007.
Int'l Search Report EP 06020584.6 dated Jan. 12, 2007.
Int'l Search Report EP 06020756.0 dated Feb. 5, 2007.
Int'l Search Report EP 06 024122.1 dated Mar. 19, 2007.
Int'l Search Report EP 06024123.9 dated Feb. 26, 2007.
Int'l Search Report EP 07 001480.8 dated Apr. 12, 2007.
Int'l Search Report EP 07 001488.1 dated May 29, 2007.
Int'l Search Report EP 07 009026.1 dated Sep. 12, 2007.
Int'l Search Report Extended—EP 07 009029.5 dated Jul. 12, 2007.
Int'l Search Report EP 07 009321.6 dated Aug. 17, 2007.
Int'l Search Report EP 07 010672.9 dated Oct. 1, 2007.
Int'l Search Report EP 07 013779.9 dated Oct. 18, 2007.
Int'l Search Report EP 07 014016 dated Jan. 28, 2008.
Int'l Search Report EP 07 015191.5 dated Dec. 19, 2007.
Int'l Search Report EP 07 015601.3 dated Dec. 6, 2007.
Int'l Search Report EP 07 020283.3 dated Jan. 16, 2008.
Int'l Search Report EP 07 021646.0 dated Jul. 9, 2008.
Int'l Search Report EP 07 021647.8 dated May 2, 2008.
Int'l Search Report EP 08 02692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report PCT/US98/18640 dated Dec. 17, 1998.
Int'l Search Report PCT/US98/23950 dated Dec. 29, 1998.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 3, 2001.
International Search Report PCT/US01/11224 dated Nov. 13, 2001.
Int'l Search Report PCT/US01/11340 dated Aug. 7, 2001.
Int'l Search Report PCT/US01/11420 dated Oct. 8, 2001.
Int'l Search Report PCT/US02/01890 dated Jul. 17, 2002.
Int'l Search Report PCT/US02/11100 dated Jul. 9, 2002.
Int'l Search Report PCT/US03/28534 dated Dec. 19, 2003.
Int'l Search Report PCT/US04/03436 dated Oct. 5, 2004.
Int'l Search Report PCT/US04/13273 dated Nov. 22, 2004.
Int'l Search Report PCT/US04/15311 dated Nov. 18, 2004.
Int'l Search Report PCT/US07/021438 dated Apr. 1, 2008.
Int'l Search Report PCT/US07/021440 dated Apr. 8, 2008.
Int'l Search Report PCT/US08/61498 dated Sep. 22, 2008.
Int'l Search Report EP 09 152267.2 Dated Jun. 15, 2009.
Int'l Search Report EP 09 152898.4 Dated Jun. 10, 2009.
Int'l Search Report PCT/US09/032690 dated Jun. 16, 2009.

* cited by examiner

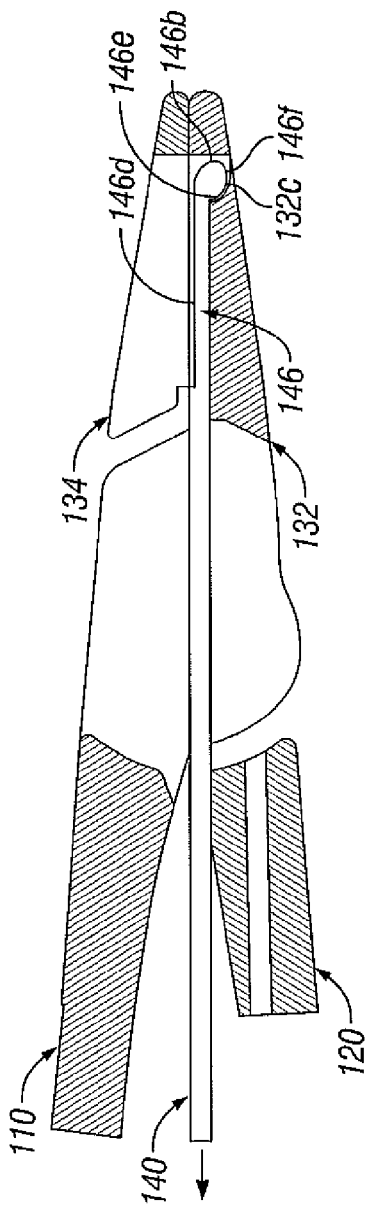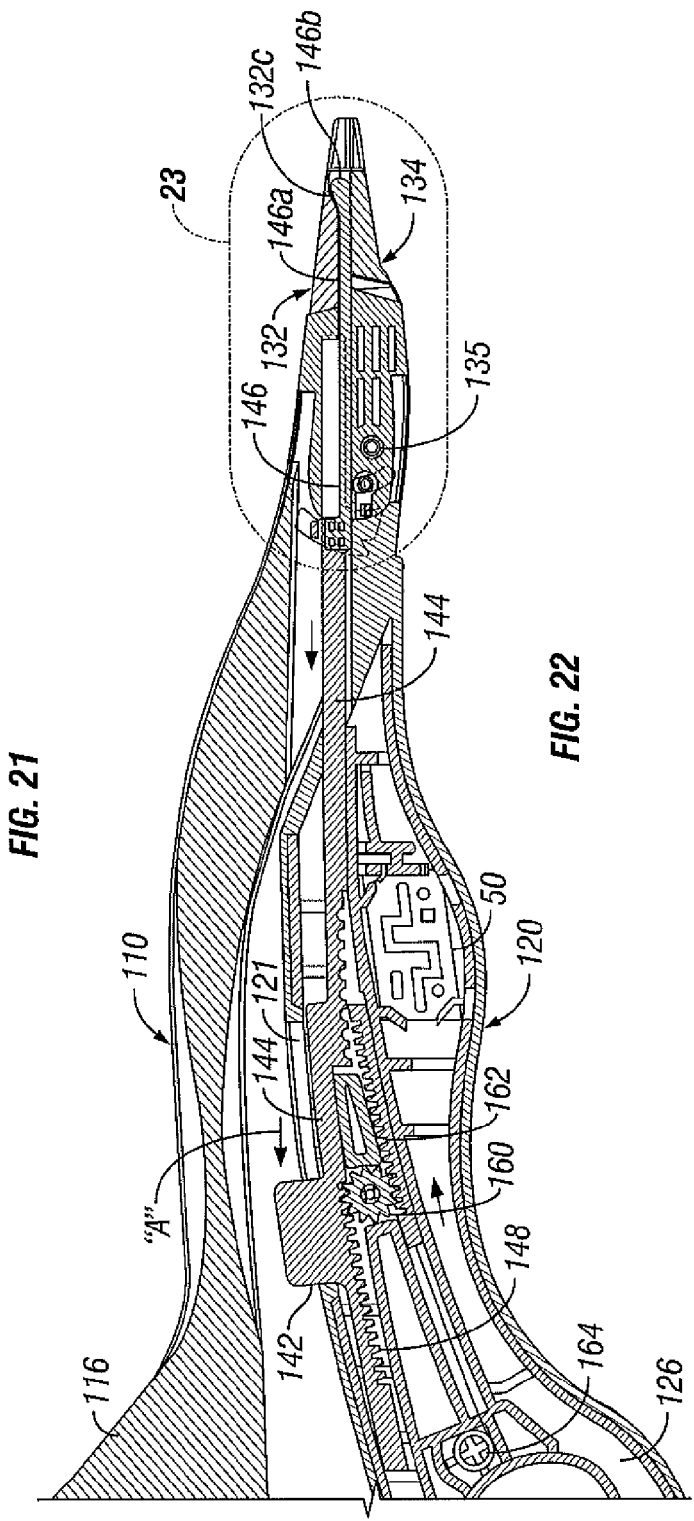

SPRING LOADED RECIPROCATING TISSUE CUTTING MECHANISM IN A FORCEPS-STYLE ELECTROSURGICAL INSTRUMENT

CROSS-REFERENCE TO RELATED APPLICATIONS

The present application is a Continuation of U.S. application Ser. No. 11/242,488, now U.S. Pat. No. 7,500,975, filed on Oct. 3, 2005, which is a Continuation-in-Part of U.S. application Ser. No. 10/991,157, now U.S. Pat. No. 7,131,970, filed on Nov. 17, 2004, which claims the benefit of priority to U.S. Provisional Patent Application Ser. No. 60/523,387, filed on Nov. 19, 2003. U.S. patent application Ser. No. 11/242,488 also claims the benefit of priority to each of U.S. Provisional Patent Application Nos. 60/616,972, filed on Oct. 8, 2004, and 60/616,968, filed on Oct. 8, 2004. All of these applications are herein incorporated by reference in their entirety.

BACKGROUND

The present disclosure relates to forceps used for open surgical procedures. More particularly, the present disclosure relates to an open forceps, having a spring loaded reciprocating tissue cutting mechanism, which applies a combination of mechanical clamping pressure and electrosurgical energy to seal tissue and which cutting mechanism is selectively activatable to sever the tissue.

TECHNICAL FIELD

A forceps is a pliers-like instrument which relies on mechanical action between its jaws to grasp, clamp and constrict vessels or tissue. So-called "open forceps" are commonly used in open surgical procedures whereas "endoscopic forceps" or "laparoscopic forceps" are, as the name implies, used for less invasive endoscopic surgical procedures. Electrosurgical forceps (open or endoscopic) utilize both mechanical clamping action and electrical energy to affect hemostasis by heating tissue and blood vessels to coagulate and/or cauterize tissue.

Certain surgical procedures require more than simply cauterizing tissue and rely on the unique combination of clamping pressure, precise electrosurgical energy control and gap distance (i.e., distance between opposing jaw members when closed about tissue) to "seal" tissue, vessels and certain vascular bundles.

Vessel sealing or tissue sealing is a recently-developed technology which utilizes a unique combination of radiofrequency energy, pressure and gap control to effectively seal or fuse tissue between two opposing jaw members or sealing plates. Vessel or tissue sealing is more than "cauterization" which is defined as the use of heat to destroy tissue (also called "diathermy" or "electrodiathermy") and vessel sealing is more than "coagulation" which is defined as a process of desiccating tissue wherein the tissue cells are ruptured and dried. "Vessel sealing" is defined as the process of liquefying the collagen, elastin and ground substances in the tissue so that it reforms into a fused mass with significantly-reduced demarcation between the opposing tissue structures.

In order to effectively "seal" tissue or vessels, two predominant mechanical parameters must be accurately controlled: 1) the pressure applied to the vessel or tissue; and 2) the gap distance between the conductive tissue contacting surfaces (electrodes). As can be appreciated, both of these parameters are affected by the thickness of the tissue being sealed. Accurate application of pressure is important for several reasons: to reduce the tissue impedance to a low enough value that allows enough electrosurgical energy through the tissue; to overcome the forces of expansion during tissue heating; and to contribute to the end tissue thickness which is an indication of a good seal. It has been determined that a good seal for certain tissues is optimum between 0.001 inches and 0.006 inches.

With respect to smaller vessels or tissue, the pressure applied becomes less relevant and the gap distance between the electrically conductive surfaces becomes more significant for effective sealing. In other words, the chances of the two electrically conductive surfaces touching during activation increases as the tissue thickness and the vessels become smaller.

Commonly owned, U.S. Pat. No. 6,511,480, PCT Patent Application Nos. PCT/US01/11420 and PCT/US01/11218, U.S. patent application Ser. Nos. 10/116,824, 10/284,562 and 10/299,650 all describe various open surgical forceps which seal tissue and vessels. All of these references are hereby incorporated by reference herein. In addition, several journal articles have disclosed methods for sealing small blood vessels using electrosurgery. An article entitled Studies on Coagulation and the Development of an Automatic Computerized Bipolar Coagulator, J. Neurosurg., Volume 75, July 1991, describes a bipolar coagulator which is used to seal small blood vessels. The article states that it is not possible to safely coagulate arteries with a diameter larger than 2 to 2.5 mm. A second article is entitled Automatically Controlled Bipolar Electrocoagulation—"COA-COMP", Neurosurg. Rev. (1984), pp. 187-190, describes a method for terminating electrosurgical power to the vessel so that charring of the vessel walls can be avoided.

Typically and particularly with respect to open electrosurgical procedures, once a vessel is sealed, the surgeon has to remove the sealing instrument from the operative site, substitute a new instrument and accurately sever the vessel along the newly formed tissue seal. As can be appreciated, this additional step may be both time consuming (particularly when sealing a significant number of vessels) and may contribute to imprecise separation of the tissue along the sealing line due to the misalignment or misplacement of the severing instrument along the center of the tissue sealing line.

Many endoscopic vessel sealing instruments have been designed which incorporate a knife or blade member which effectively severs the tissue after forming a tissue seal. For example, commonly-owned U.S. application Ser. Nos. 10/116,944 and 10/179,863 describe one such endoscopic instrument which effectively seals and cuts tissue along the tissue seal. Other instruments include blade members or shearing members which simply cut tissue in a mechanical and/or electromechanical manner and are relatively ineffective for vessel sealing purposes.

There exists a need to develop an open electrosurgical forceps which is simple, reliable and inexpensive to manufacture and which effectively seals tissue and vessels and which allows a surgeon to utilize the same instrument to effectively sever the tissue along the newly formed tissue seal.

SUMMARY

According to an aspect of the present disclosure, there is provided an open electrosurgical forceps for sealing tissue. The forceps have a pair of first and second shaft portions each having a jaw member disposed at a distal end thereof. The jaw members are movable from a first position in spaced relation relative to one another to at least one subsequent position. In that position, the jaw members cooperate to grasp tissue therebetween. The forceps also have each jaw member including an electrically conductive sealing surface which communicates electrosurgical energy through tissue held therebetween. At least one of the jaw members include a knife slot defined along a length thereof with the knife slot dimensioned to reciprocate a knife blade therein. The forceps also have a cutting mechanism for selectively actuating the knife blade from a first position wherein the knife blade is disposed at least substantially entirely within the knife slot of one jaw member to at least one subsequent position wherein the knife blade is at least partially deployed from the knife slot of the same jaw member. The knife blade is displaceable in a direction substantially transverse to a longitudinal axis of the forceps.

According to another aspect of the present disclosure, the open electrosurgical forceps have the cutting mechanism with a drive rod extending through a channel formed in at least one of the first and second shaft portions. The drive rod includes a distal end operatively connected with the knife blade and the forceps have a tab operatively connected to the drive rod for manipulating the drive rod in order to displace the knife blade between the first and the at least one subsequent positions.

According to still another aspect of the present disclosure, the open electrosurgical forceps have the knife blade with a first edge defining a cutting edge and a second edge, opposite the first edge, defining a camming surface. The camming surface of the knife blade engages a corresponding camming surface formed in the slot of the jaw member to effectuate displacement of the knife blade between the first and the at least one subsequent positions.

According to another aspect of the present disclosure, the open electrosurgical forceps have a first edge of the knife blade residing in close proximity to the sealing surface when the knife blade is in the first position.

According to another aspect of the present disclosure, the open electrosurgical forceps have a slot of the jaw member defining a camming surface. The camming surface is configured to complement the camming surface of the knife blade.

According to another aspect of the present disclosure, the open electrosurgical forceps have the drive rod. The drive rod is displaced in a proximal direction with the camming surface of the knife blade engaging the camming surface of the slot formed in the jaw member to displace the knife blade from the first position to the at least one subsequent position.

According to yet another aspect of the present disclosure, the open electrosurgical forceps have a biasing member. The biasing member is for urging the drive rod to a distal most position.

According to still yet another aspect of the present disclosure, the open electrosurgical forceps have a hand switch. The hand switch is operatively associated therewith and provides a user with the ability to selectively apply electrosurgical energy.

According to another aspect of the present disclosure, the open electrosurgical forceps have a cable electrically interconnecting the forceps to a source of electrosurgical energy. The cable has a first lead electrically connected directly to a second of the jaw members and a second and third lead electrically connected to the hand switch.

According to another aspect of the present disclosure, the open electrosurgical forceps have the knife blade fabricated from a material capable of transmitting compressive and tensile forces or fabricated from spring steel.

According to another aspect of the present disclosure, the open electrosurgical forceps have each jaw member being arcuate.

According to another aspect of the present disclosure, the open electrosurgical forceps have the slot formed in the respective jaw member being arcuate.

According to another aspect of the present disclosure, the open electrosurgical forceps have the drive rod with a first rack formed therein. The first rack of the drive rod operatively engages a pinion gear rotatably supported in the second shaft portion.

According to another aspect of the present disclosure, the open electrosurgical forceps have a second gear rack slidably supported in the second shaft portion and operatively engaged with the pinion gear.

According to yet still another aspect of the present disclosure, the open electrosurgical forceps have a proximal displacement of the drive rod resulting in a distal displacement of the second gear rack.

According to another aspect of the present disclosure, the open electrosurgical forceps have a biasing member operatively connected to the second gear rack. The biasing member is for maintaining the second gear rack in a proximal-most position.

According to another aspect of the present disclosure, the open electrosurgical forceps have first and second shaft portions pivotable with respect to one another.

According to another aspect of the present disclosure, the open electrosurgical forceps with proximal displacement of the cutting mechanism results in the displacement of the knife blade in a direction having a longitudinal component of displacement and an orthogonal component of displacement. These displacements are relative to the longitudinal axis of the forceps.

According to another aspect of the present disclosure, the open electrosurgical forceps have the knife blade made from a biocompatible material.

According to another aspect of the present disclosure, the open electrosurgical forceps have a pair of first and second shaft portions with each having a jaw member disposed at a distal end thereof. The jaw members are movable from a first position in spaced relation relative to one another to at least one subsequent position wherein the jaw members cooperate to grasp tissue therebetween. The forceps have each jaw member including an electrically conductive sealing surface which communicates electrosurgical energy through tissue held therebetween and at least one of the jaw members including a slot defined along a length thereof. The slot is dimensioned to reciprocate a knife blade therefrom. The forceps also have a cutting mechanism which selectively actuates the knife blade from a first position to a second position. The knife blade is disposed at least substantially entirely within the knife slot of the jaw member in the first position and the knife blade moves distally from the first position to the second position in a cutting stroke. The knife blade partially deploys from the knife slot of the jaw member from the first position to the second position during the cutting stroke. The knife blade further moves in a direction perpendicular to a longitudinal axis of the jaw members from the first position to the second position during the cutting stroke when the jaw members are in the subsequent position.

According to another aspect of the present disclosure, the movement of the knife from the first position to the second position during the cutting stroke places the knife blade under tensile stress. Movement of the knife blade from the first position to the second position during the cutting stroke does not compress the knife blade.

According to another aspect of the present disclosure, the open electrosurgical forceps have a pair of first and second shaft portions each having a jaw member disposed at a distal end thereof. The jaw members are movable from a first position in spaced relation relative to one another to at least one subsequent position wherein the jaw members cooperate to grasp tissue therebetween with each of said jaw members including an electrically conductive sealing surface which communicates electrosurgical energy through tissue held therebetween and at least one of the jaw members including a slot. The slot is defined along a length thereof and is dimensioned to reciprocate a knife blade therein. The knife blade has a complementary size to fit in the length of the slot. The forceps also have a cutting mechanism which selectively actuates the knife blade from a first position to a second position in a cutting stroke. The knife blade partially deploys from the knife slot of the jaw member from the first position to the second position during the cutting stroke and the knife blade cuts the sealed tissue during a first stroke in a direction from a proximal location to a distal location when the jaw members are disposed in the subsequent position.

According to another aspect of the present disclosure, the open electrosurgical forceps have the knife blade with an edge. The edge is pulled along the sealed tissue from the proximal location to the distal location upon the knife blade being deployed.

According to another aspect of the present disclosure, the open electrosurgical forceps have the cutting stroke which moves the knife from the proximal location to the distal location being actuated by a switch. This provides convenience to the surgeon.

BRIEF DESCRIPTION OF THE DRAWINGS

Various embodiments of the subject instrument are described herein with reference to the following drawing figures. It should be understood, however, that the drawings are designed for the purpose of illustration only and not as a definition of the limits of the invention.

FIG. 21 is a side, schematic elevational view of the end effector of the forceps of FIGS. 1-31 with the cutting mechanism in a retracted position;

FIG. 22 is a side, elevational view of the forceps of FIGS. 1-3, while in the closed position, illustrating actuation of the cutting mechanism;

DETAILED DESCRIPTION

Figure 1:
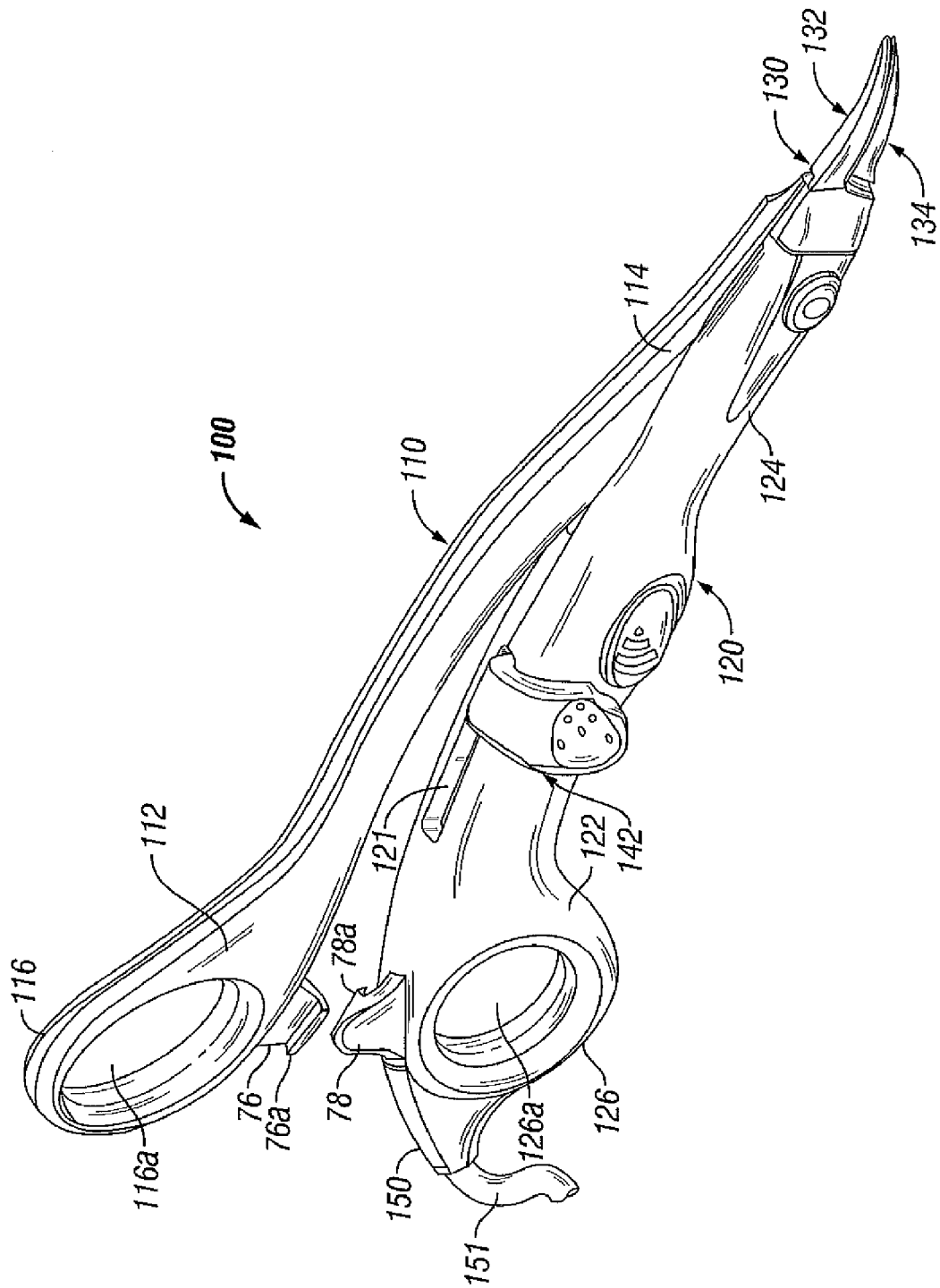
FIG. 1 is a left, perspective view of an open forceps according to an embodiment of the present disclosure.
Figure 2:
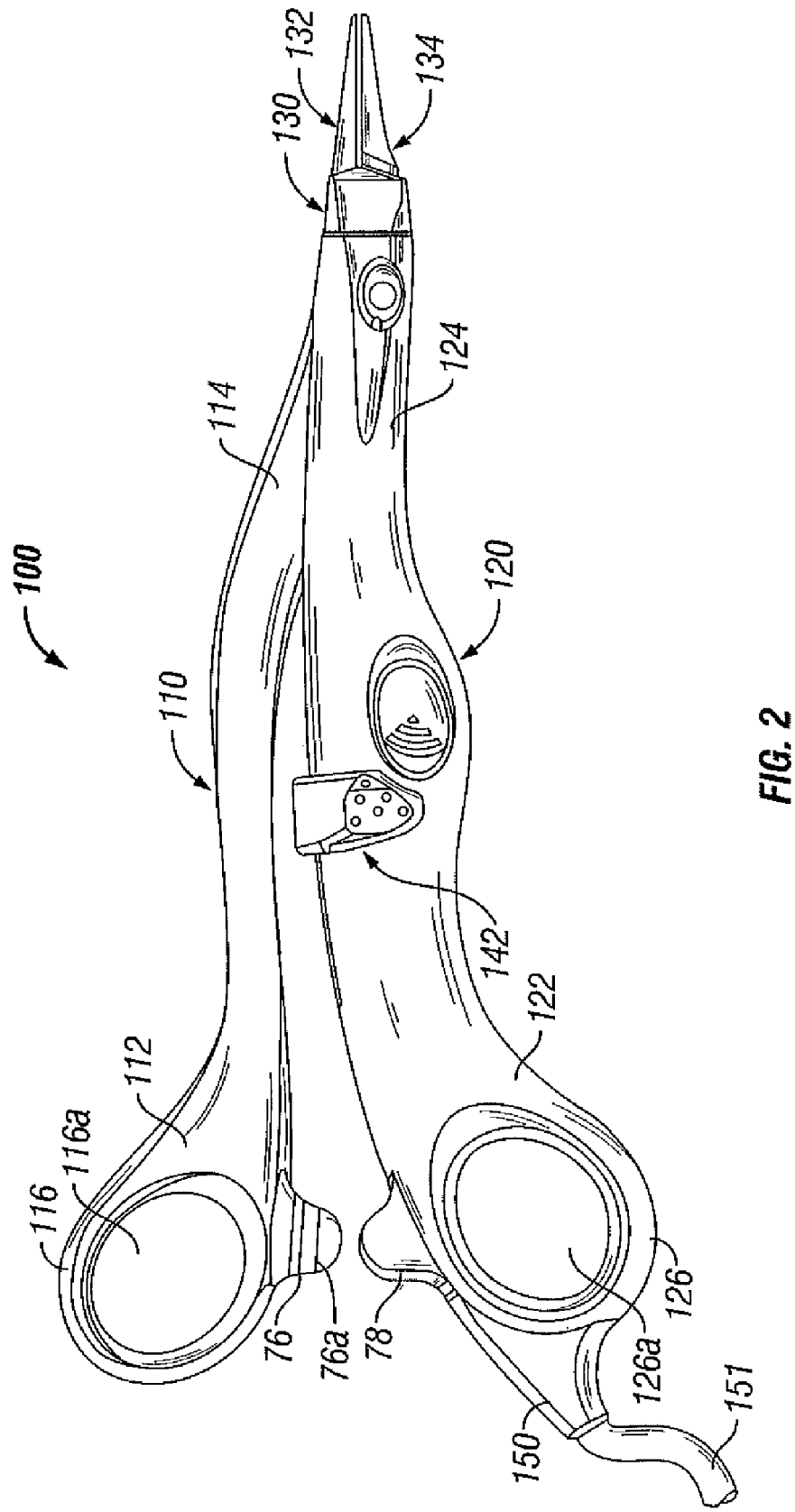
FIG. 2 is a left, side view of the forceps of FIG. 1.

Referring now to FIGS. 1-13, a forceps or hemostat for use in open surgical procedures, preferably, open electrosurgical procedures, is generally designated as 100. Forceps 100 includes a first elongated shaft portion 110 and a second elongated shaft portion 120. Each shaft portion 110, 120 includes a proximal end 112 and 122, respectively, and a distal end 114, 124, respectively. In the drawings and in the descriptions which follow, the term "proximal", as is traditional, will refer to the end of forceps 100 which is closer to the user, while the term "distal" will refer to the end which is further from the user.

Forceps 100 includes an end effector assembly 130 which attaches to distal ends 114, 124 of shaft portions 110, 120, respectively. As explained in more detail below, end effector assembly 130 includes a pair of opposing jaw members 132, 134 which are pivotably connected about a pivot pin 135 (see FIG. 7) and which are movable relative to one another to grasp tissue therebetween.

Preferably, each shaft portion 110 and 120 includes a handle 116, 126, respectively, disposed at proximal ends 112, 122, thereof. Each handle 116, 126 defines a finger hole 116a, 126a, respectively, therethrough for receiving a finger of the user. As can be appreciated, finger holes 116a, 126a, facilitate movement of shaft portions 110 and 120 relative to one another which, in turn, pivot the jaw members 132 and 134, about pivot pin 135, from an open position wherein the jaw members 132 and 134 are disposed in spaced relation relative to one another to a clamping or closed position wherein jaw members 132 and 134 cooperate to grasp tissue therebetween.

Figure 3:
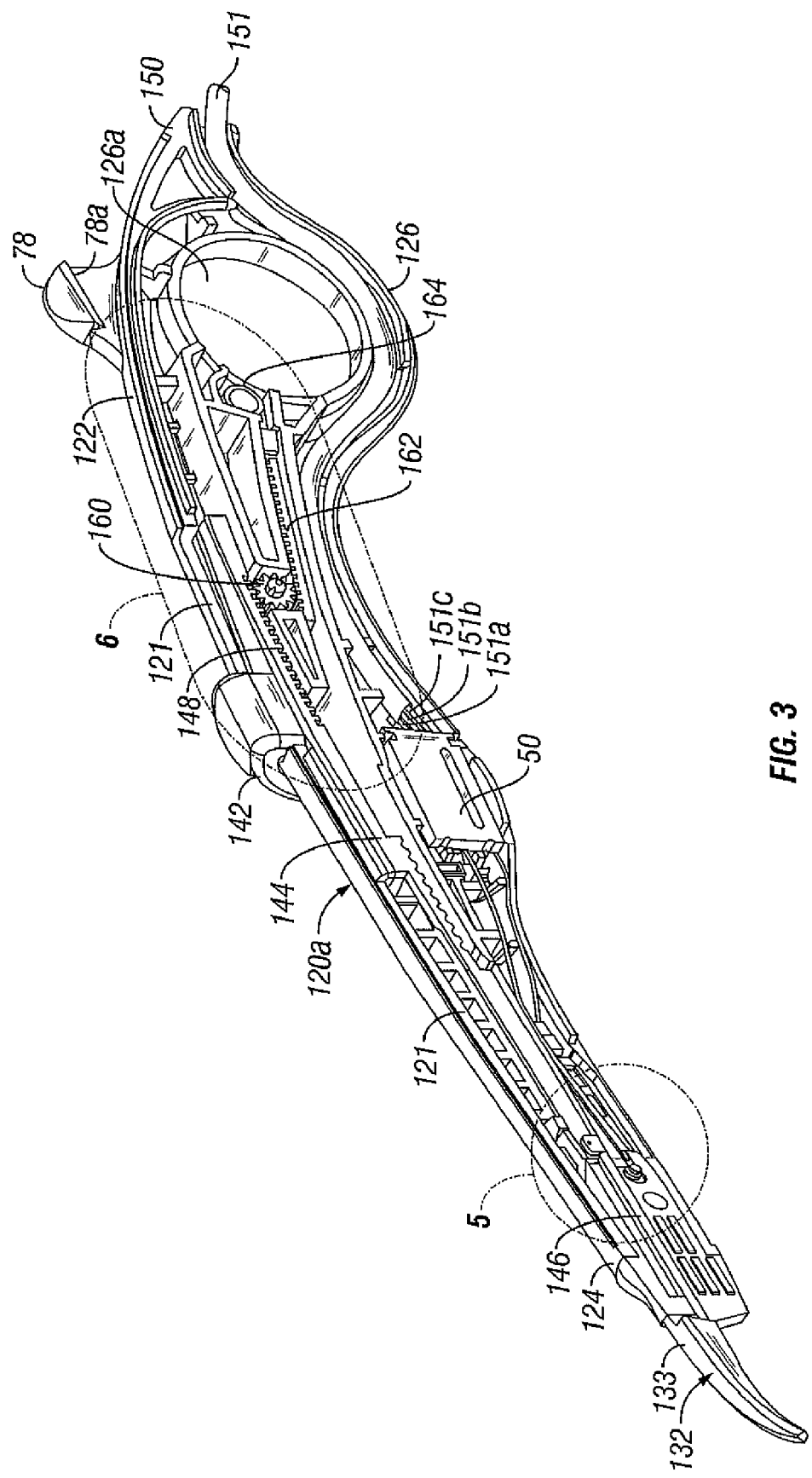
FIG. 3 is an internal, perspective view of the forceps of FIGS. 1 and 2, showing an actuating mechanism for deploying a cutter.
Figure 7:
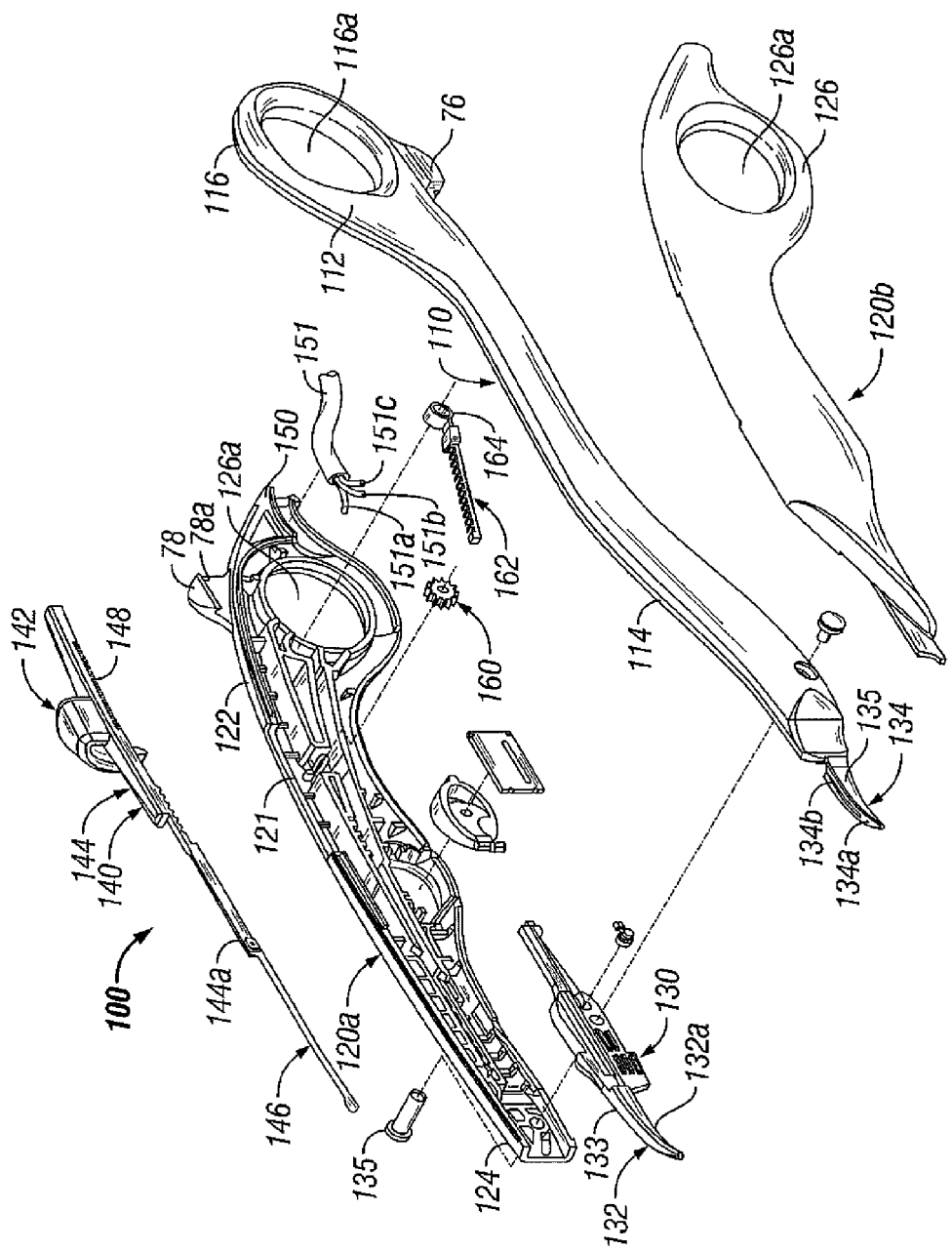
FIG. 7 is an exploded perspective view of the forceps of FIGS. 1-3.
Figure 8:
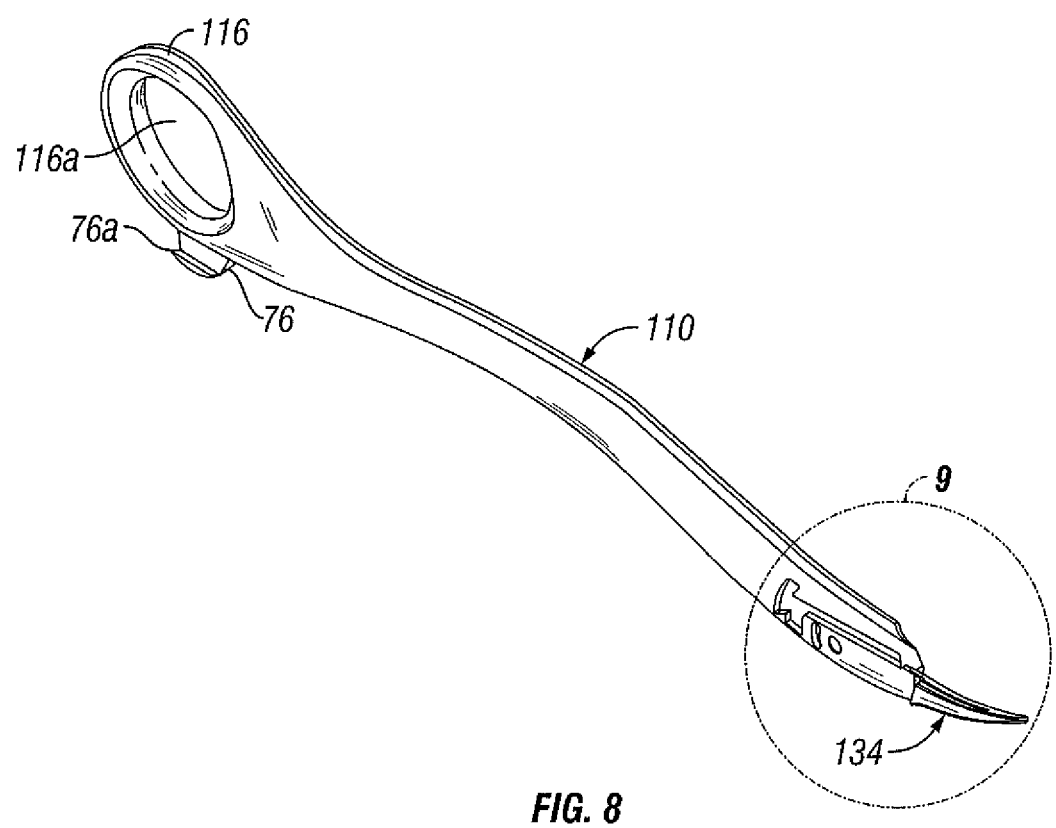
FIG. 8 is a left, side perspective view of a shaft portion of the forceps of FIGS. 1-3.

As best seen in FIGS. 1, 3 and 7, second shaft portion 120 is bifurcated to define an elongated channel 121 therealong which is dimensioned to receive first shaft portion 110 therein. More particularly, second shaft portion 120 is made from two halves 120a, 120b (see FIG. 7) which are matingly engaged during assembly to form second shaft portion 120 and to define elongated channel 121. It is envisioned that the two halves 120a, 120b may be secured to one another by sonic welding at a plurality of different points along the perimeter thereof of the two housing halves 120a, 120b may be mechanically engaged in any other known fashion, including and not limited to, snap-fitting, gluing, screwing, and the like. During assembly, first shaft portion 110 is positioned within second shaft portion 120 and secured about pivot pin 135 which allows first and second shaft portions 110 and 120 to pivot with respect to one another.

As seen in FIGS. 1-3 and 7, one of shaft portions 110, 120, e.g., second shaft portion 120, includes a proximal shaft connector 150 which is designed to connect forceps 100 to a source of electrosurgical energy, e.g., an electrosurgical generator (not shown). Connector 150 electromechanically engages an electrosurgical conducting cable 151 such that the user may selectively apply electrosurgical energy as needed. Alternatively, cable 151 may be fed directly into second shaft portion 120 as best seen in FIG. 3.

As explained in more detail below, the distal end of cable 151 connects to a handswitch 50 to permit the user to selectively apply electrosurgical energy, as needed, to seal tissue grasped between jaw members 132, 134. More particularly, the interior of cable 151 houses leads 151a, 151b and 151c which upon activation of handswitch 50 conduct the different electrical potentials from the electrosurgical generator to jaw members 132, 134. As can be appreciated, positioning handswitch 50 on forceps 100 gives the user more visual and tactile control over the application of electrosurgical energy. These aspects are explained below with respect to the discussion of handswitch 50 and the electrical connections associated therewith.

As briefly discussed above, jaw members 132, 134 of end effector assembly 130 are selectively pivotable about pivot pin 135 from the open position, for receiving tissue therebetween, to the closed position, for grasping tissue therebetween. Jaw members 132 and 134 are generally symmetrical and include similar component features which cooperate to permit facile rotation about pivot pin 135 to affect the grasping and sealing of tissue. As a result and unless otherwise noted, jaw member 132 and the operative features associated therewith are initially described herein in detail and the similar component features with respect to jaw member 134 will be briefly summarized thereafter. Moreover, many of the features of jaw members 132 and 134 are described in detail in commonly-owned U.S. patent application Ser. Nos. 10/284, 562, 10/116,824, 09/425,696, 09/178,027 and PCT Application Serial No. PCT/US01/11420 the contents of which are all hereby incorporated by reference in their entirety herein.

Figure 15:
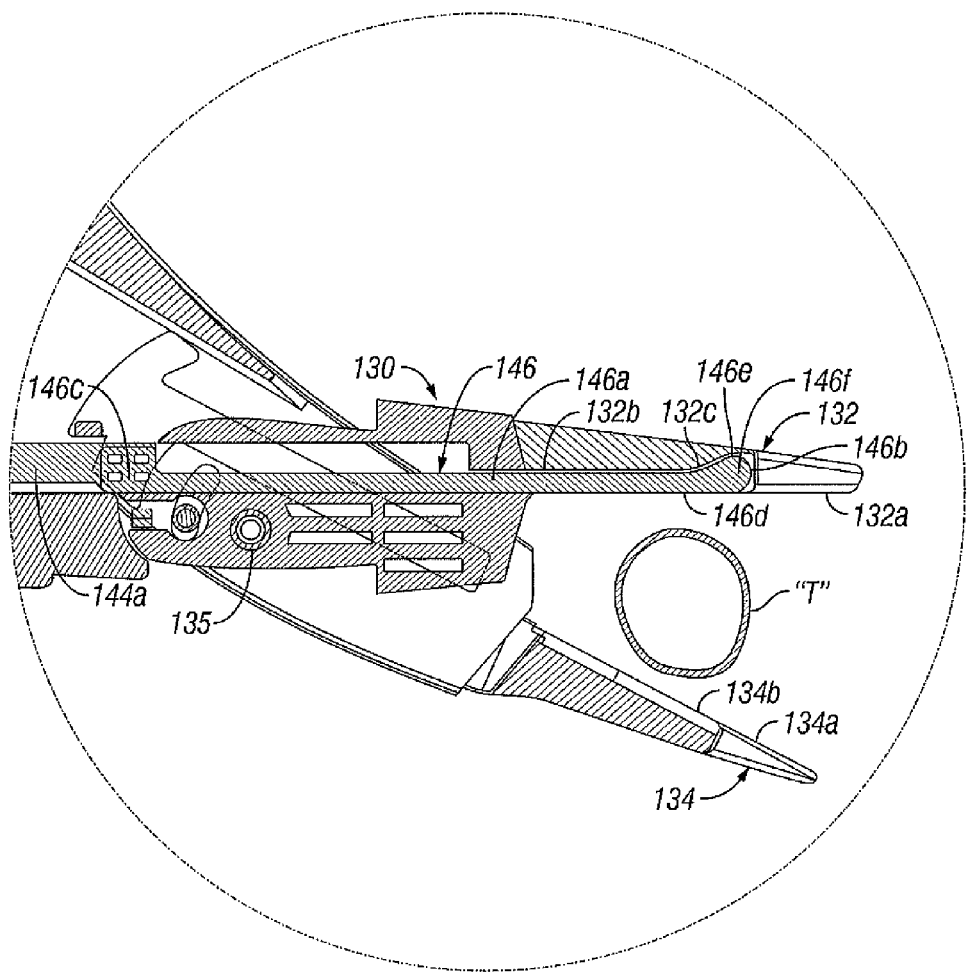
FIG. 15 is an enlarged cross-sectional view of the area indicated as 15 of FIG. 14.
Figure 16:
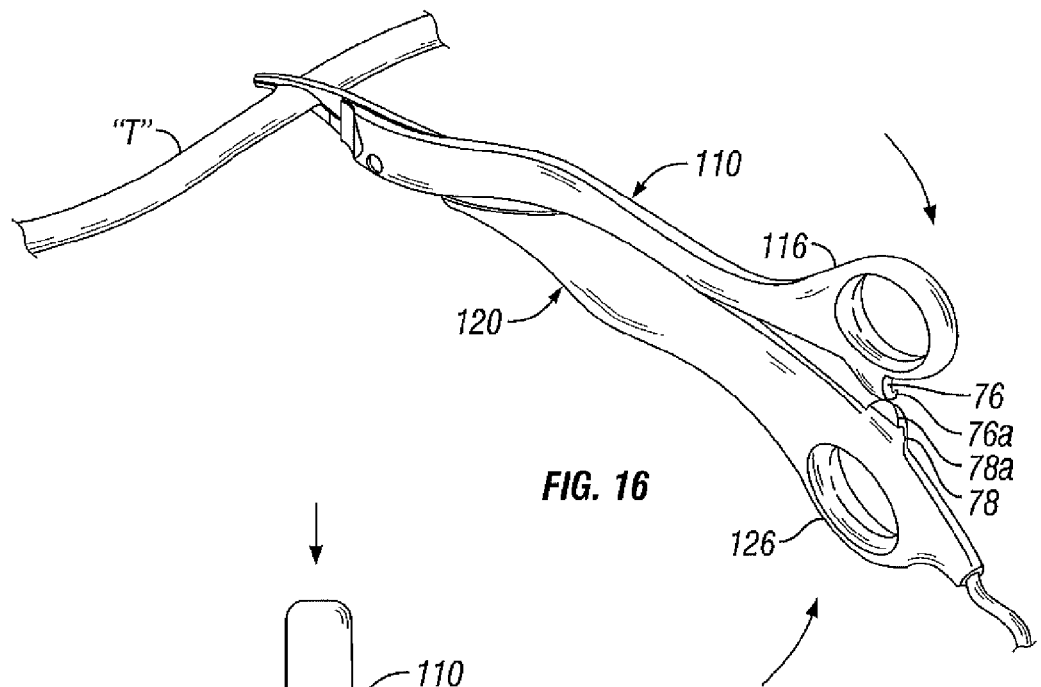
FIG. 16 is a rear, perspective view of the forceps of FIGS. 1-3, illustrating the operation thereof.
Figure 17:
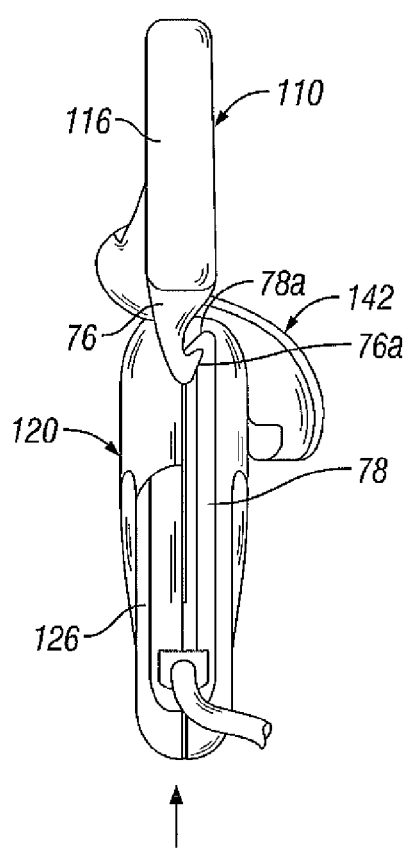
FIG. 17 is a rear, end view of the forceps of FIGS. 1-3, illustrating the inter-engagement of the ratchet interfaces of the respective shaft members.
Figure 18:
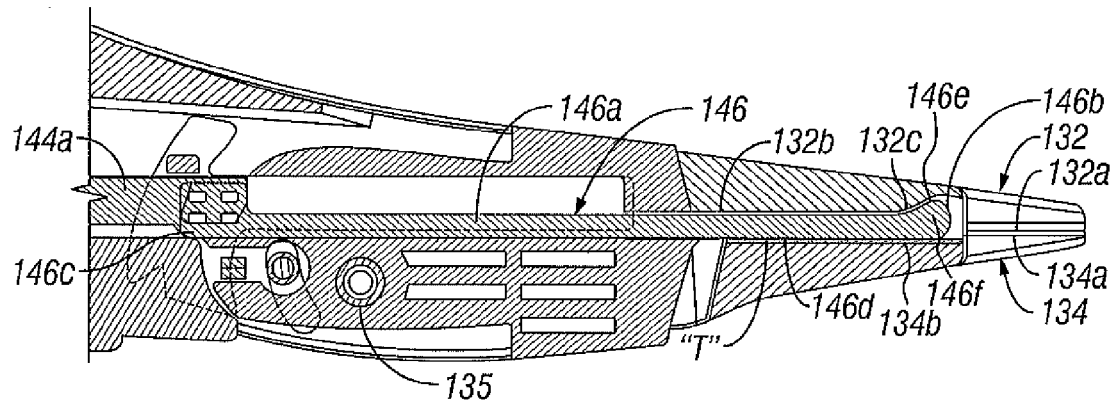
FIG. 18 is an enlarged cross-sectional view of the area indicated as 15 of FIG. 14 of the forceps of FIGS. 1-3, as taken through a plane which is orthogonal to the pivot axis of first and second jaw members, illustrating the forceps in a closed condition.
Figure 19:
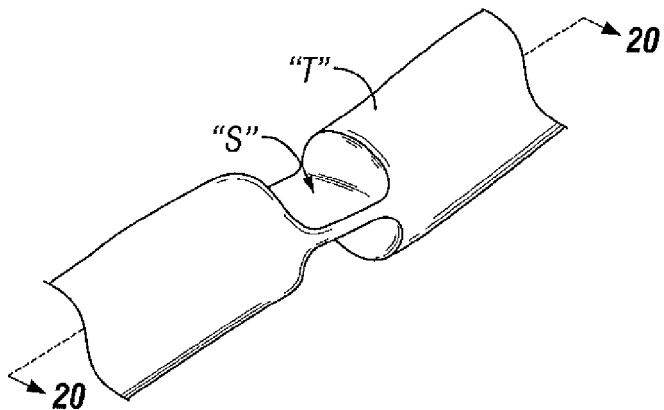
FIG. 19 is a perspective exemplary illustration of a vessel following the sealing thereof with the forceps of FIGS. 1-3.
Figure 20:
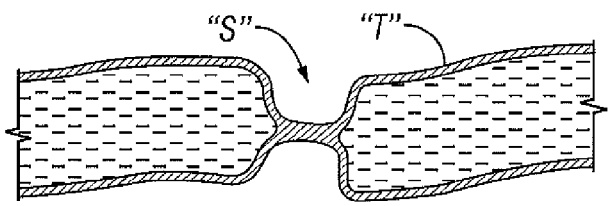
FIG. 20 is a longitudinal, cross-sectional view of the vessel of FIG. 19 as taken through 20-20 of FIG. 19.
Figure 23:
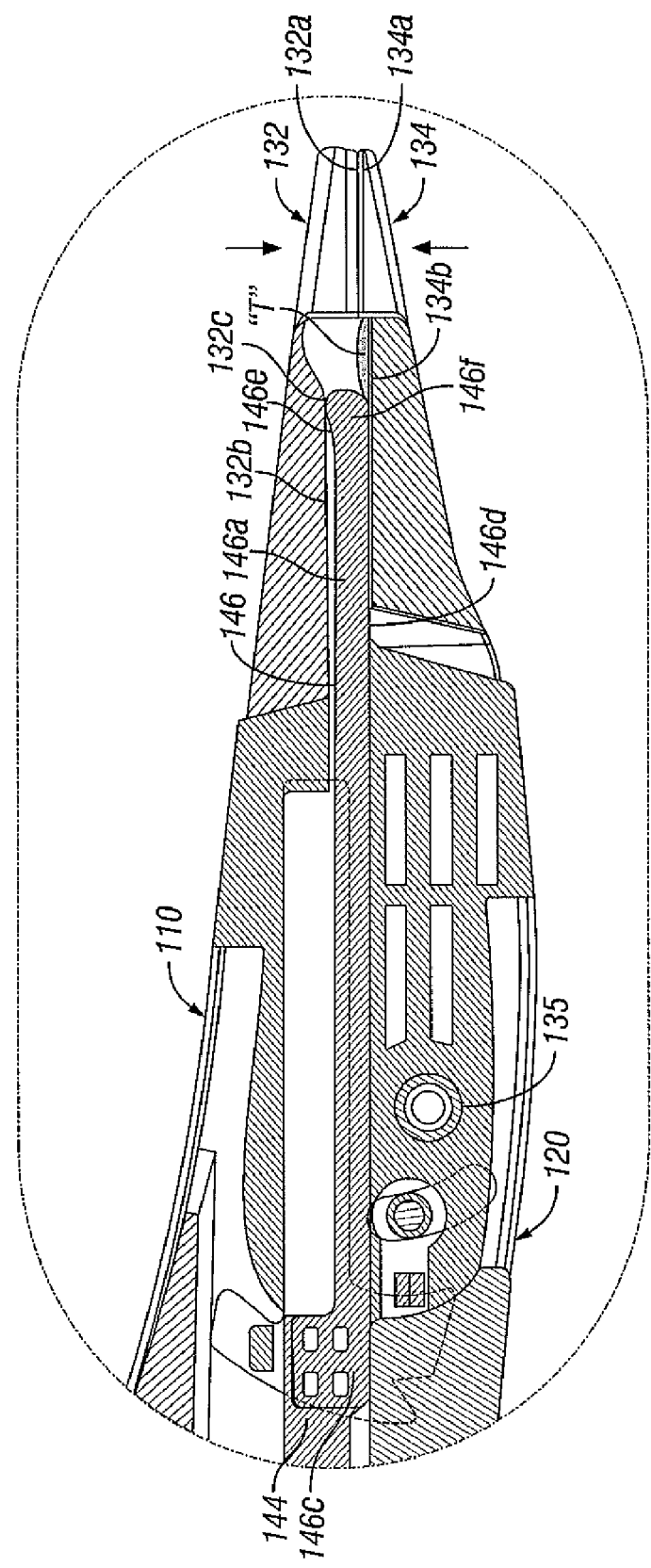
FIG. 23 is an enlarged, view of the area indicated as 23 of FIG. 22.
Figure 24:
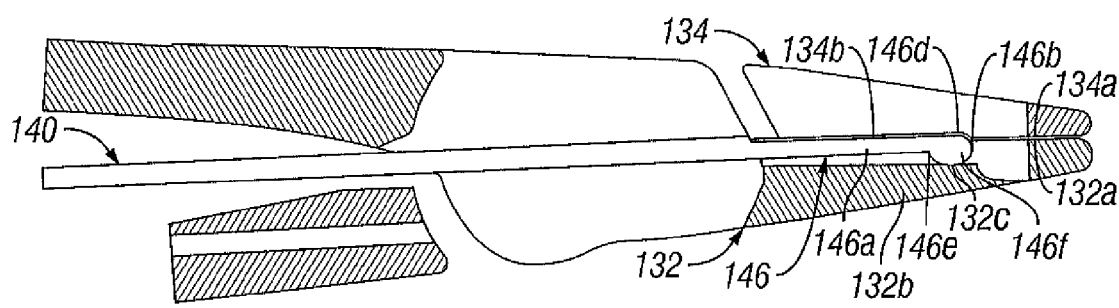
FIG. 24 is a side, schematic elevational view of the end effector of the forceps of FIGS. 1-31 with the cutting mechanism in an actuated position.
Figure 25:
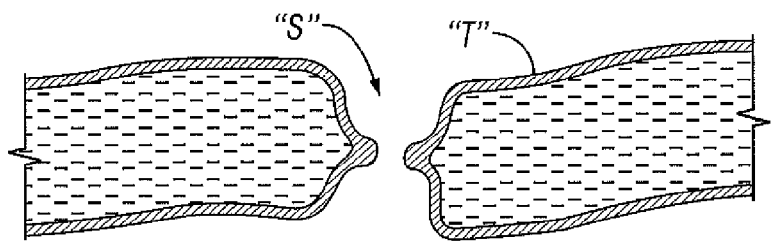
FIG. 25 is a longitudinal, cross-sectional view of the vessel of FIG. 19, as taken through 20-20 of FIG. 19, following cutting of with the cutting mechanism.

Jaw member 132 includes an insulated outer housing 133 which is dimensioned to mechanically engage an electrically conductive sealing surface 132a (see FIG. 15). Insulated outer housing 133 extends along the entire length of jaw member 132 to reduce alternate or stray current paths during sealing and/or incidental burning of tissue. The electrically conductive sealing surface 132a conducts electrosurgical energy of a first potential to the tissue upon activation of handswitch 50. Insulated outer housing 133 is dimensioned to securely engage the electrically conductive sealing surface 132a. It is envisioned that this may be accomplished by stamping, by overmolding, by overmolding a stamped electrically conductive sealing plate and/or by overmolding a metal injection molded seal plate. Other methods of affixing electrically conductive sealing surface 132a to insulated outer housing 133 are described in detail in one or more of the above-identified references.

It is also envisioned that the electrically conductive sealing surface 132a may include a pinch trim (not shown) which facilitates secure engagement of the electrically conductive sealing surface 132a to the insulated outer housing 133 and also simplifies the overall manufacturing process. It is also contemplated that the electrically conductive sealing surface 132a may include an outer peripheral edge which has a radius and the insulated outer housing 133 meets the electrically conductive sealing surface 132a along an adjoining edge which is generally tangential to the radius and/or meets along the radius. Preferably, at the interface, the electrically conductive sealing surface 132a is raised relative to the insulated outer housing 133. These and other envisioned embodiments are discussed in commonly-owned, co-pending PCT Application Serial No. PCT/US01/11412 and commonly owned, co-pending PCT Application Serial No. PCT/US01/11411, the contents of both of these applications being incorporated by reference herein in their entirety.

Preferably, the insulated outer housing 133 and the electrically conductive sealing surface 132a are dimensioned to limit and/or reduce many of the known undesirable effects related to tissue sealing, e.g., flashover, thermal spread and stray current dissipation. All of the aforementioned and cross referenced manufacturing techniques produce an electrode having an electrically conductive sealing surface 132a which is substantially surrounded by an insulated outer housing 133.

Likewise, as seen in FIG. 7, jaw member 134 includes similar elements which include: an outer housing 135 which engages an electrically conductive sealing surface 134a. The electrically conductive sealing surface 134a conducts electrosurgical energy of a second potential to the tissue upon activation of the handswitch 50.

It is envisioned that one of the jaw members, e.g., 132, includes at least one stop member (not shown) disposed on the inner facing surface of the electrically conductive sealing surface 132a (and/or 134a). Alternatively or in addition, the stop member(s) may be positioned adjacent to the electrically conductive sealing surfaces 132a, 134a or proximate the pivot pin 135. The stop member(s) is/are preferably designed to facilitate gripping and manipulation of tissue and to define a gap between opposing jaw members 132 and 134 during sealing. Preferably the separation distance during sealing or the gap distance is within the range of about 0.001 inches (~0.03 millimeters) to about 0.006 inches (~0.016 millimeters).

A detailed discussion of these and other envisioned stop members as well as various manufacturing and assembling processes for attaching, disposing, depositing and/or affixing the stop members to the electrically conductive sealing surfaces 132a, 134a are described in commonly-assigned, co-pending PCT Application Serial No. PCT/US01/11222 which is hereby incorporated by reference in its entirety herein.

As mentioned above, two mechanical factors play an important role in determining the resulting thickness of the sealed tissue and effectiveness of the seal, i.e., the pressure applied between opposing jaw members 132 and 134 and the size of the gap between opposing jaw members 132 and 134 (or opposing sealing surface 132a and 134a during activation). It is known that the thickness of the resulting tissue seal cannot be adequately controlled by force alone. In other words, too much force and jaw members 132 and 134 may touch and possibly short resulting in little energy traveling through the tissue thus resulting in an inadequate seal. Too little force and the seal would be too thick. Applying the correct force is also important for other reasons: to oppose the walls of the vessel; to reduce the tissue impedance to a low enough value that allows enough current through the tissue; and to overcome the forces of expansion during tissue heating in addition to contributing towards creating the required end tissue thickness which is an indication of a good seal.

Preferably, sealing surfaces 132a and 134a are relatively flat to avoid current concentrations at sharp edges and to avoid arcing between high points. In addition, and due to the reaction force of the tissue when engaged, jaw members 132 and 134 are preferably manufactured to resist bending, i.e., tapered along their length to provide a constant pressure for a constant tissue thickness at parallel and the thicker proximal portion of jaw members 132 and 134 will resist bending due to the reaction force of the tissue.

Figure 9:
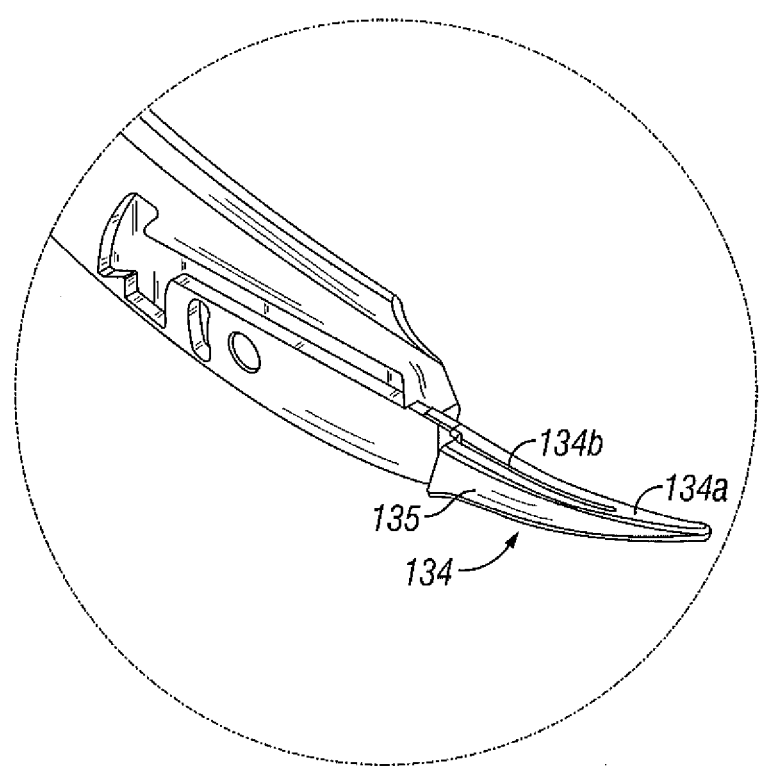
FIG. 9 is an enlarged perspective view of the area indicated as 9 of FIG. 8.
Figure 10:
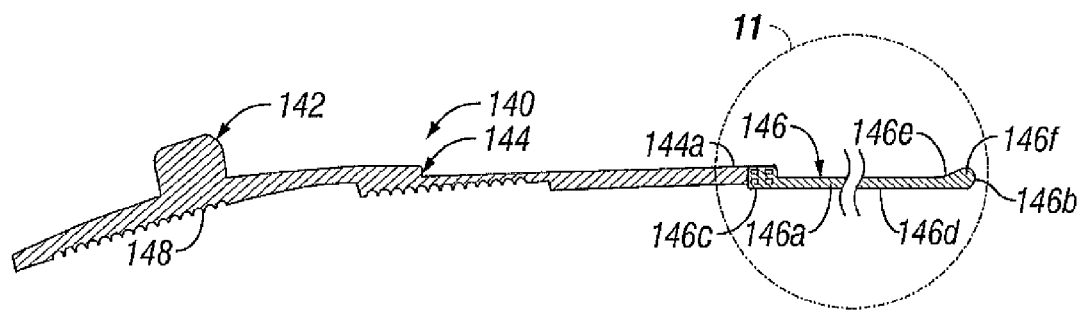
FIG. 10 is a side view of the cutter of the present disclosure.
Figure 11:
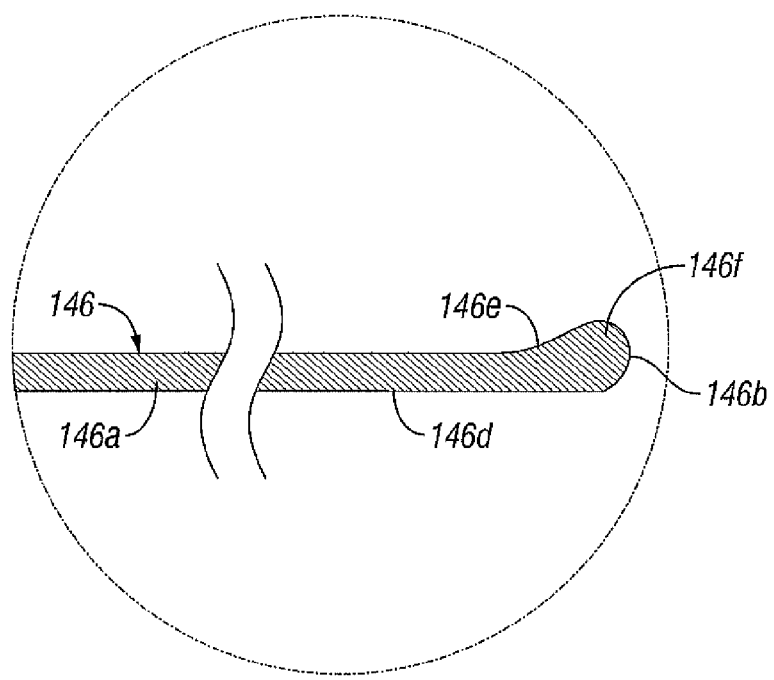
FIG. 11 is an enlarged view of the area indicated as 11 of FIG. 10.
Figure 12:
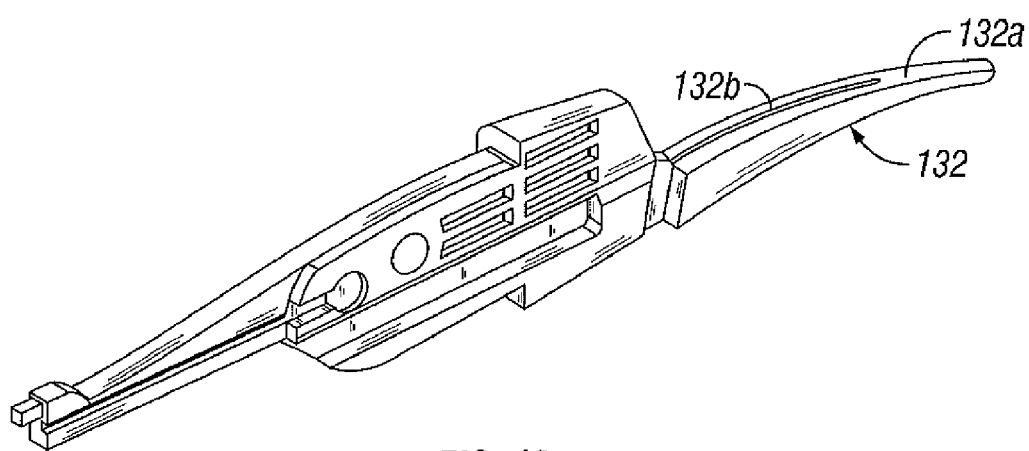
FIG. 12 is a right, side perspective view of a jaw member of the forceps of FIGS. 1-3.
Figure 13:
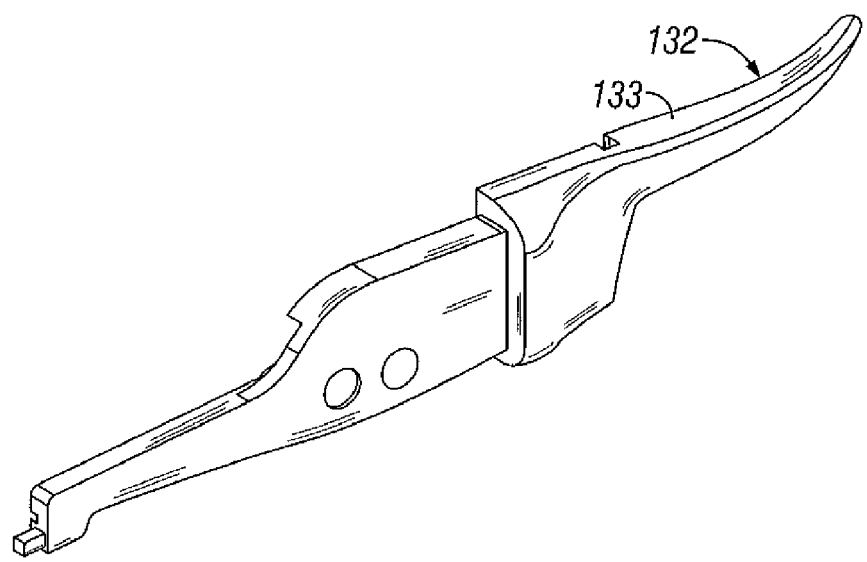
FIG. 13 is a left, side perspective view of the jaw member of FIG. 12.

As best seen in FIGS. 7, 9 and 12, each jaw member 132, 134 includes a knife slot 132b, 134b disposed therebetween (i.e., formed in respective sealing surfaces 132a, 134a thereof) which is configured to allow reciprocation of a cutting mechanism 140 therewithin. One example of a knife slot is disclosed in commonly-owned U.S. patent application Ser. No. 10/284,562, the entire contents of which are hereby incorporated by reference herein. Preferably, the complete knife slot is formed when two opposing knife slots 132b, 134b come together upon grasping of the tissue. It is envisioned that the knife slot may be tapered or some other configuration which facilitates or enhances cutting of the tissue during reciprocation of cutting mechanism 140 in the proximal and distal directions. Moreover, the knife channel may be formed with one or more safety features which prevent cutting mechanism 140 from advancing through and/or otherwise slicing tissue until jaw members 132, 134 are closed onto the tissue.

For example, a lockout mechanism, operatively associated with cutting mechanism 140, may be provided to prevent advancement of cutting mechanism 140 until jaw embers 132, 134 are positioned about the tissue to be treated. Examples of lockout mechanisms and features are described in commonly-owned U.S. application Ser. Nos. 10/460,926, 10/461,550 and 10/462,121, which are all incorporated by reference herein in their entirety.

Figure 4:
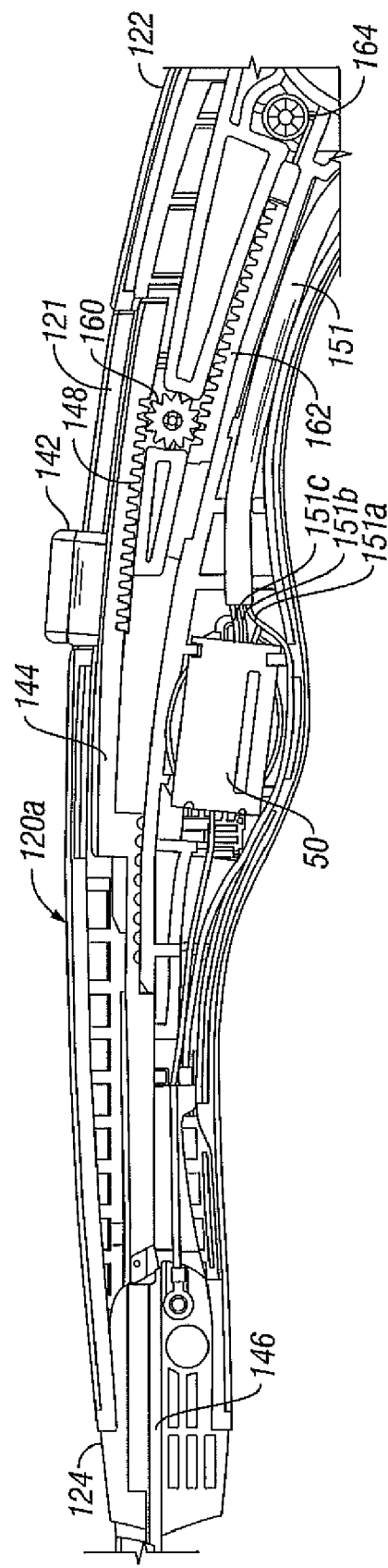
FIG. 4 is an internal, side view of the forceps of FIGS. 1-3, showing the actuating mechanism for deploying the cutter.
Figure 5:
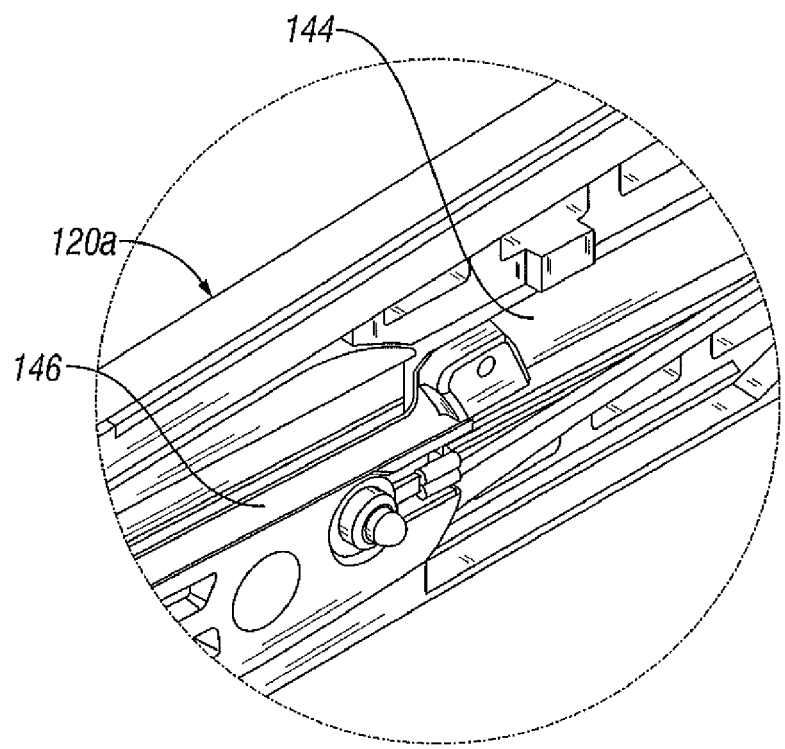
FIG. 5 is an enlarged perspective view of the area indicated as 5 in FIG. 3.
Figure 6:
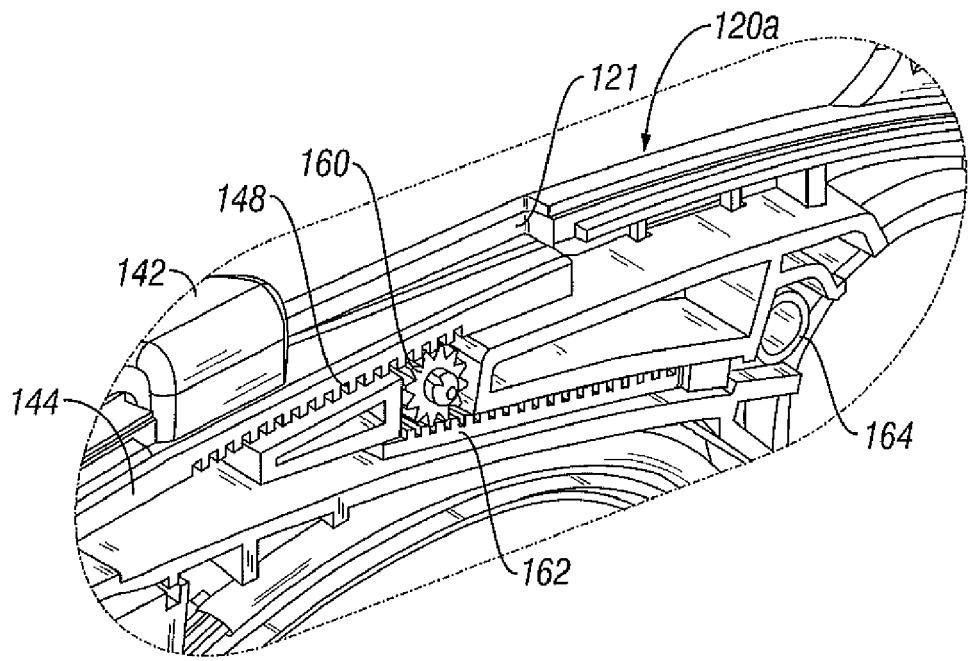
FIG. 6 is an enlarged perspective view of the area indicated as 6 of FIG. 3.

As best shown in FIGS. 3, 4 and 7, the arrangement of first shaft portion 110 is different from second shaft portion 120. More particularly, second shaft portion 120 is hollow to define a chamber therein, which chamber is dimensioned to house both handswitch 50 (and the electrical components associated therewith as explained in more detail below) and cutting mechanism 140.

As best seen in FIGS. 4-7, 10 and 11, cutting mechanism 140 includes a finger tab 142 which is operatively associated with a drive rod 144 such that movement of finger tab 142 moves drive rod 144 in a corresponding direction within second shaft portion 120. Preferably, finger tab 142 extends from elongated slot 121 formed in second shaft portion 120. Drive rod 144 includes a distal end 144a which is configured to mechanically support a knife blade 146 thereto.

Desirably, drive rod 144 defines a first gear track or rack 148 formed in a surface thereof. In one embodiment, it is envisioned that a pinion gear 160 may be rotatably supported in second shaft portion 120 so as to operatively engage first rack 148 of drive rod 144. A second gear rack 162 may be slidably supported in second shaft portion 120 so as to also operatively engage pinion gear 160. Pinion gear 160 is interdisposed between first gear rack 148 and second gear rack 162 so as to mechanically mesh both gear racks 148 and 162 with one another and convert proximal displacement of drive rod 144 into distal translation of second gear rack 162 and vice versa. More particularly, when the user pulls finger tab 142 in a proximal direction, as represented by arrow "A" of FIG. 22, the drive rod 144 is translated proximally which, in turn, rotates pinion gear 160. Rotation of pinion gear 160, in turn, forces second rack 162 to translate in a distal direction.

It is envisioned that multiple gears or gears with different gear ratios may be employed to reduce surgical fatigue which may be associated with actuating cutting mechanism 140. In addition, it is contemplated that racks 148 and 162 may be of different length to provide additional mechanical advantage for advancing the jaw members through the tissue. Desirably, the rack and pinion arrangement may be curved for spatial purposes and to facilitate handling and/or to enhance the overall ergonomics of the forceps 10.

Preferably, a biasing member 164 (e.g., a coil spring) is operatively connected to second gear rack 162 in such a manner that biasing member 164 tends to draw and/or bias second gear rack 162 to a proximal-most position and, in turn, tends to press and/or bias drive rod 142 to a distal-most position. As will be described in greater detail below, biasing member 164 automatically returns drive rod 144 to an un-advanced position and, in turn, return knife blade 146 to the retracted position. A biasing member may be operatively associated with drive rod 144 and/or second gear rack 162 in any manner so as to achieve the same purpose.

Preferably, drive rod 144 is made from a flexible sheet or band of metal or plastic which does not buckle upon forward movement thereof. In other words, drive rod 144 is fabricated from a flexible material capable of transmitted both compressive and tensile forces. For example, drive rod 144 may be fabricated from spring steel.

Preferably, finger tab 142 includes one or more ergonomically friendly features which enhance the tactile feel and grip of the user to facilitate actuation of finger tab 142. Such features may include, raised protuberances, rubber inserts, scallops and gripping surfaces, and the like.

As seen in FIGS. 7, 10, 11, 15, 18, 21, 23 and 24, knife blade 146 includes an elongate body portion 146a having a distal end 146b and a proximal end 146c. Preferably, proximal end 146c of knife blade 146 is configured to mechanically engage distal end 144a of drive rod 144. Knife blade 146 defines a first edge 146d forming the cutting edge of knife blade 146 and a second edge 146e, opposite first edge 146d, defining a camming surface or bulge 146f. Preferably, knife blade 146 is disposed in knife slot 132b of first jaw member 132 such that first edge 146d of knife blade 146 is oriented toward tissue contacting surface 132a. As such, knife blade 146 is seated in knife slot 132b such that camming surface 146f of second edge 146e is operatively associated with a camming surface 132c formed in knife slot 132b of first jaw member 132.

As will be described in greater detail below, as cutting mechanism 140 is drawn in a proximal direction (e.g., in the direction of arrow "A" of FIG. 22), knife blade 146 is also drawn in a proximal direction. In so doing, camming surface 146f of second edge 146e of knife blade 146 engages and/or otherwise rides against camming surface 132c formed in knife slot 132b of first jaw member 132. As such, distal end 146b and, in turn, first edge 146d of knife blade 146 is urged out of knife slot 132b of first jaw member 132 and towards knife slot 134b of second jaw member 134. Due to the resiliency of knife blade 146, as cutting mechanism 140 is driven in a distal direction, knife blade 146 and, in turn, first edge 146d of knife blade 146 is retracted into knife slot 132b.

Camming surface 146f of second edge 146e of knife blade 146 engages with camming surface 132c of knife slot 132b in order to displace knife blade 146 in a direction which is transverse to a longitudinal axis of forceps 100, preferably transverse to a longitudinal axis of second shaft portion 120. In other words, longitudinal displacement of finger tab 142 results in knife blade 146 displacing in a direction having a component of displacement which is parallel to the longitudinal axis and a component of displacement which is orthogonal to the longitudinal axis. This results in knife blade 146 cutting tissue with a slicing action and/or motion.

As seen in FIGS. 1-3, 7, 8, 16 and 17, forceps 100 may include a ratchet for selectively locking jaw members 132, 134 relative to one another at various positions during pivoting. A first ratchet interface 76 preferably extends from proximal end 112 of first shaft portion 110 towards a second ratchet interface 78 preferably extending from proximal end 122 of second shaft portion 120, in a generally vertically aligned manner such that the inner facing surfaces of each ratchet 76 and 78 abut one another upon closure about the tissue. Preferably, each ratchet interface 76, 78 includes a plurality of flanges 76a, 78a, respectively, (in the interest of clarity, only one flange is shown) which project from the inner facing surface of each ratchet interface 76 and 78 such that the ratchet interfaces 76a, 78a interlock in at least one position.

Preferably, each position associated with the cooperating ratchet interfaces 76a, 78a hold a specific, i.e., constant, strain energy in the shaft portions 110, 120, which, in turn, transmits a specific closing force to jaw members 132, 134. It is envisioned that the ratchet may include graduations or other visual markings which enable the user to easily and quickly ascertain and control the amount of closure force desired between jaw members 132, 134.

As seen in FIG. 4, the electrical details relating to switch 50 are shown in greater detail. More particularly, and as mentioned above, cable 150 includes three electrical leads 151a-151c which are fed through second shaft portion 120. Cable 150 is fed into the bottom or proximal end of second shaft portion 120 and is held securely therein by one or more mechanical interfaces (not shown). Lead 151c extends directly from cable 150 and connects to jaw member 134 to conduct the second electrical potential thereto. Leads 151a, 151b extend from cable 150 and connect to the hand switch or joy-stick-like toggle switch 50.

Several different types of handswitches 50 are envisioned, for example, one particular type of handswitch is disclosed in commonly-owned, co-pending U.S. patent application Ser. No. 10/460,926, the entire contents of which are hereby incorporated by reference herein.

Electrical leads 151a and 151b are electrically connected to switch 50. When switch 50 is depressed, a trigger lead carries the first electrical potential from switch 50 to first jaw member 132. As mentioned above, the second electrical potential is carried by lead 151c directly from the generator (not shown) to second jaw member 134. It is envisioned that a safety switch or circuit (not shown) may be employed such that switch 50 cannot fire unless jaw members 132 and 134 are closed and/or unless jaw members 132 and 134 have tissue held therebetween. In the latter instance, a sensor (not shown) may be employed to determine if tissue is held therebetween. In addition, other sensor mechanisms may be employed which determine pre-surgical, concurrent surgical (i.e., during surgery) and/or post surgical conditions. The sensor mechanisms may also be utilized with a closed-loop feedback system coupled to the electrosurgical generator to regulate the electrosurgical energy based upon one or more pre-surgical, concurrent surgical or post surgical conditions. Various sensor mechanisms and feedback systems are described in commonly-owned, co-pending U.S. patent application Ser. No. 10/427,832 the entire contents of which are hereby incorporated by reference herein.

Preferably, jaw members 132 and 134 are electrically isolated from one another such that electrosurgical energy can be effectively transferred through the tissue to form a tissue seal. Preferably, each jaw member, e.g., 132, includes a uniquely-designed electrosurgical cable path disposed therethrough which transmits electrosurgical energy to the electrically conductive sealing surface 132a. It is envisioned that jaw member 132 may include one or more cable guides or crimp-like electrical connectors to direct the cable lead towards electrically conductive sealing surface 132a. Preferably, the cable lead is held loosely but securely along the cable path to permit pivoting of jaw member 132 about pivot pin 135.

Desirably, as seen in FIG. 7, cable leads 151a-151c are protected by two insulative layers, an outer protective sheath which surrounds all three leads 151a-151c and a secondary protective sheath which surrounds each individual cable lead 151a-151c. The two electrical potentials are isolated from one another by virtue of the insulative sheathing surrounding each cable lead 151a-151c.

Turning now to FIGS. 14-25, in operation, the surgeon simply utilizes the two opposing handles 116, 126 to approximate and grasp tissue between jaw members 132, 134. The surgeon then activates handswitch 50 (or in certain instances a footswitch, not shown) to provide electrosurgical energy to each jaw member 132, 134 to communicate energy through the tissue held therebetween. Once sealed, the surgeon activates cutting mechanism 140 to deploy knife blade 146 to slice through the treated tissue to sever and divide the tissue along the tissue seal.

Figure 14:
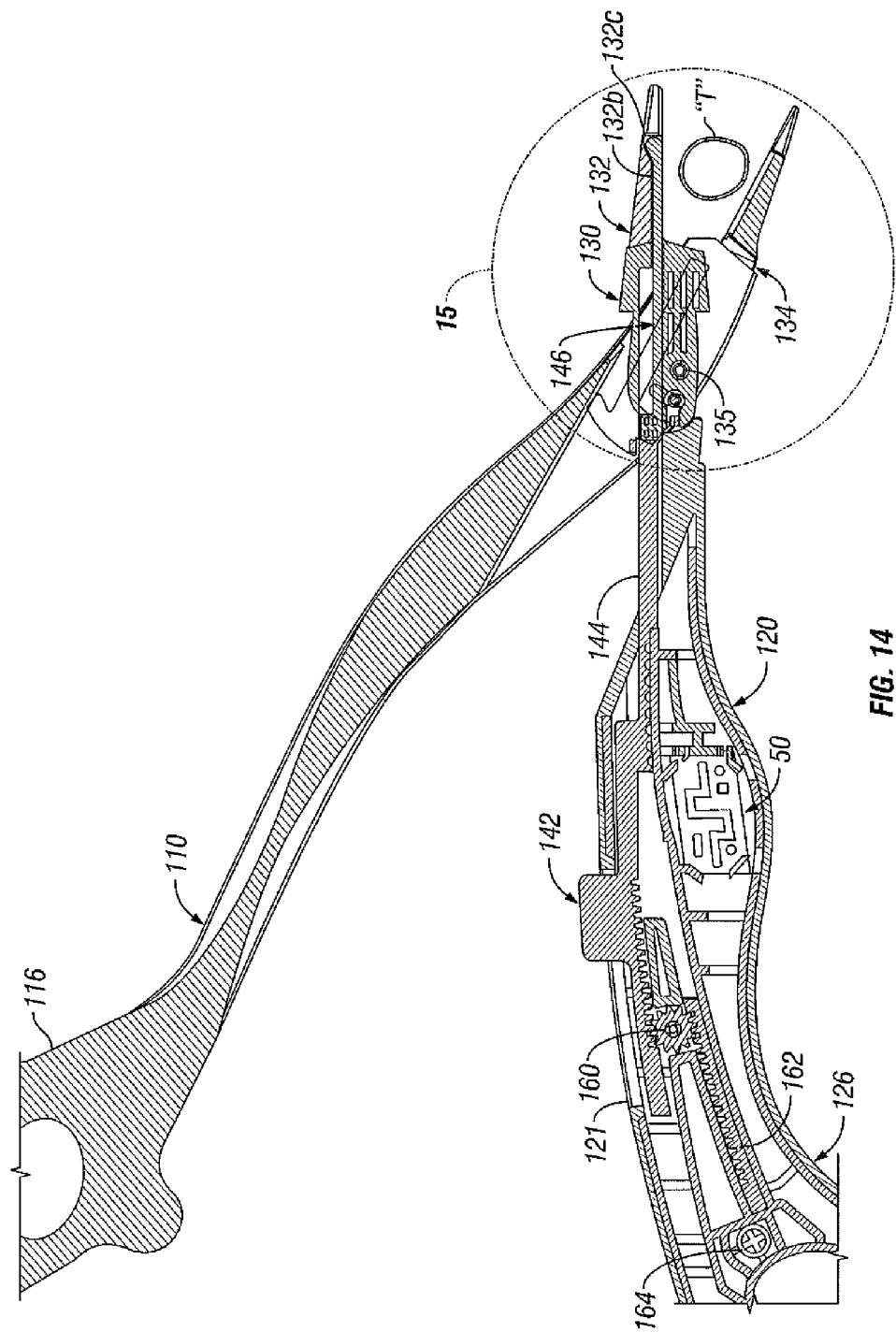
FIG. 14 is a cross-sectional view of the forceps of FIGS. 1-3, as taken through a plane which is orthogonal to the pivot axis of first and second jaw members, illustrating the forceps in an open condition.

In particular, as seen in FIGS. 14 and 15, with forceps 100 in the open condition, the surgeon positions end effector 130 of forceps 100, in the operative field, such that the tissue to be treated "T" is disposed between jaw members 132, 134. As seen in FIGS. 16-22, the surgeon then squeezes (i.e., approximates) opposing handles 116, 126 to thereby close jaw members 132, 134 onto tissue "T". Desirably, flange 76a of first ratchet interface 76 may be interlocked with flange 78a of second ratchet interface 78 in order to transmit a specific closing force to jaw members 132, 134. The surgeon then activates handswitch 50 to provide electrosurgical energy to each jaw member 132, 134 and to communicate energy through tissue "T" held therebetween and to effectively seal tissue "T" at "S", see FIGS. 19 and 20.

Once tissue "T" has been sealed at "S", as seen in FIGS. 21-24, the surgeon may, if desired and/or necessary, activate cutting mechanism 140. As described above, cutting mechanism 140 is activated by withdrawing on finger tab 142 in a proximal direction (i.e., in the direction of arrow "A") which, in turn, draws knife blade 146 in a proximal direction. In so doing, the camming surface of second edge 146e of knife blade 146 engages and/or otherwise rides against camming surface 132c formed in knife slot 132b of first jaw member 132. As such, distal end 146b and, in turn, first edge 146d of knife blade 146 is urged out of knife slot 132b of first jaw member 132 and towards knife slot 134b of second jaw member 134 to thereby cut, slice and/or otherwise divide tissue "T" at "S".

Following the cutting action, the surgeon may displace finger tab 142 in a distal direction in order to return knife blade 146 to knife slot 132b. In particular, knife blade 146 and, in turn, first edge 146d of knife blade 146 is retracted into knife slot 132b.

From the foregoing and with reference to the various figure drawings, those skilled in the art will appreciate that certain modifications can also be made to the present disclosure without departing from the scope of the same. For example, none of the afore described forceps require that the tissue be necessarily cut after sealing or that the tissue be sealed prior to cutting. As can be appreciated, this gives the user additional flexibility when using the instrument.

For example, it is also contemplated that forceps 100 (and/or the electrosurgical generator used in connection therewith) may include a sensor or feedback mechanism (not shown) which automatically selects the appropriate amount of electrosurgical energy to effectively seal the particularly-sized tissue grasped between jaw members 132 and 134. The sensor or feedback mechanism may also measure the impedance across the tissue during sealing and provide an indicator (visual and/or audible) that an effective seal has been created between jaw members 132 and 134. Commonly-owned U.S. patent application Ser. No. 10/073,761, filed on Feb. 11, 2002, entitled "Vessel Sealing System"; U.S. patent application Ser. No. 10/626,390, filed on Jul. 24, 2003, entitled "Vessel Sealing System"; U.S. patent application Ser. No. 10/427,832, filed on May 1, 2003, entitled "Method and System for Controlling Output of RF Medical Generator"; U.S. patent application Ser. No. 10/761,524, filed on Jan. 21, 2004, entitled "Vessel Sealing System"; U.S. Provisional Application No. 60/539,804, filed on Jan. 27, 2004, entitled "Method of Tissue Fusion of Soft Tissue by Controlling ES Output Along Optimal Impedance Curve"; U.S. Provisional Application No. 60/466,954; filed on May 1, 2003, entitled "Method and System for Programming and Controlling an Electrosurgical Generator System"; and U.S. Pat. No. 6,398,779, disclose several different types of sensory feedback mechanisms and algorithms which may be utilized for this purpose. The contents of these applications are hereby incorporated by reference herein.

Experimental results suggest that the magnitude of pressure exerted on the tissue by the sealing surfaces of jaw members 132 and 134 are important in assuring a proper surgical outcome. Tissue pressures within a working range of about 3 $kg/cm^2$ to about 16 $kg/cm^2$ and, preferably, within a working range of 7 $kg/cm^2$ to 13 $kg/cm^2$ have been shown to be effective for sealing arteries and vascular bundles. Tissue pressures within the range of about 4 $kg/cm^2$ to about 6.5 $kg/cm^2$ have proven to be particularly effective in sealing arteries and tissue bundles.

In one embodiment, shaft portions 110, 120 are manufactured such that the spring constant of shaft portions 110, 120, in conjunction with the placement of the ratchet interfaces 76a, 78a, will yield pressures within the above working range. In addition, the successive positions of the ratchet interfaces (if provided) increase the pressure between opposing sealing surfaces incrementally within the above working range.

Also, although the electrical connections are preferably incorporated within second shaft portion 120 and forceps 100 is intended for right-handed use, it is contemplated that the electrical connections may be incorporated within first shaft portion 110 depending upon a particular purpose and/or to facilitate manipulation by a left-handed user.

It is also envisioned that drive rod 142 may be connected to the same or alternate source of electrosurgical energy and may be selectively energizable by the surgeon during cutting. As can be appreciated, this would enable the surgeon to electrosurgically cut tissue "T" along the tissue seal at "S". As a result thereof, a substantially dull blade may be employed to electrosurgically cut tissue "T".

It is also envisioned that a substantially dull knife blade may be utilized for cutting mechanism 140 which, due to the clamping pressure between the opposing jaw members 132, 134 and due to the force with which knife blade 146 is urged out of knife slot 132a, tissue "T" will sever along the tissue seal at "S".

In one embodiment, a sealing and cutting mechanism is utilized which is selectively attachable to a conventional forceps. In other words, the sealing and cutting mechanisms are disposable which shaft portions 110, 120 are reposable. The disposable sealing and cutting mechanisms, along with their respective electrosurgical elements, simply mount atop one or both shafts of a conventional forceps to enable the surgeon to seal and cut tissue.

In one embodiment, knife blade 146 is desirably flexible to advance through a curved knife channel. For example, upon distal or proximal displacement of the cutting mechanism, the knife blade will simply flex and ride around the knife slot through the tissue held therebetween by the jaw members. It is also contemplated that the forceps may include a safety blade return mechanism (not shown). For example and as mentioned above, cutting mechanism 140 may include one of more biasing members which automatically return the knife blade to the retracted position after actuation thereof. In addition, a manual return may be included which allows the user to manually return knife blade 146 if the automatic blade return (e.g., biasing member) should fail due to sticking, skewing, or some other unforeseen surgical condition. Should the automatic return fail, the surgeon simply has to displace finger tab 142 in a distal direction to drive cutting mechanism forward and retract knife blade 146 into slot 132a of jaw member 132. A significant advantage of the present disclosure is that movement of the knife from a first position to a second position during a cutting stroke places the knife blade under tensile stress. The movement of the knife from the first position to the second position during the cutting stroke also does not compress the knife. This arrangement is very conducive as any compressive stress on the knife is disfavored greatly as this compressive stress may break the knife. Also, the movement of the knife from the first position to the second position during a cutting stroke placing the knife blade under tensile stress promotes using the knife edge instead of another chopping motion that places strain on the knife. The tensile stress is more conducive to a more natural motion of the knife for cutting, and is advantageous over any other types of devices.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of preferred embodiments. Those skilled in the art will envision other modifications within the scope and spirit of the claims appended hereto.

What is claimed is:

1. An open electrosurgical forceps for sealing tissue, comprising:
  a pair of first and second shaft portions each having a jaw member disposed at a distal end thereof, said jaw members being movable from a first position in spaced relation relative to one another to at least one subsequent position wherein the jaw members cooperate to grasp tissue therebetween, each jaw member defining a longitudinal axis;

each of said jaw members including an electrically conductive sealing surface which communicates electrosurgical energy through tissue held therein;

at least one of the jaw members including a knife slot defined along a length thereof;

a knife blade reciprocally disposed in the knife slot for deployment therefrom, the knife blade defining a cutting edge oriented substantially parallel to the longitudinal axis of the respective jaw member, wherein the knife blade includes a camming surface opposite the cutting edge, wherein the camming surface of the knife blade engages a corresponding camming surface formed in the slot of the jaw member to effectuate displacement of the knife blade between a first position and at least one subsequent position; and a cutting mechanism for selectively actuating the knife blade from the first position wherein the knife blade is disposed at least substantially entirely within the knife slot of one jaw member to the at least one subsequent position wherein the knife blade is at least partially deployed from the knife slot of the same jaw member, wherein the cutting edge of the knife blade remains substantially parallel to the longitudinal axis of the respective jaw member during actuation thereof from the first position to the at least one subsequent position to thereby slice tissue disposed between the jaw members.

2. The open electrosurgical forceps according to claim 1, wherein as the knife blade is actuated from the first position to the at least one subsequent position the camming surface of the knife blade engages the camming surface of the slot formed in the jaw member to displace the knife blade in a direction substantially transverse to the longitudinal axis of the respective jaw member.

3. The open electrosurgical forceps according to claim 2, wherein as the knife blade is actuated from the first position to the at least one subsequent position the camming surface of the knife blade engages the camming surface of the slot formed in the jaw member to displace the knife blade in a direction having a longitudinal component of translation.

4. The open electrosurgical forceps according to claim 1, wherein the cutting mechanism selectively actuates the knife blade from a first distal position to at least one subsequent proximal position.

5. The open electrosurgical forceps according to claim 1, wherein the knife blade is fabricated from a material capable of transmitting compressive and tensile forces.

6. The open electrosurgical forceps according to claim 5, wherein each jaw member is arcuate.

7. The open electrosurgical forceps according to claim 6, wherein the slot formed in the respective jaw member is arcuate.

8. An open electrosurgical forceps for sealing tissue, comprising:

a pair of first and second shaft portions each having a jaw member disposed at a distal end thereof, said jaw members being movable from a first position in spaced relation relative to one another to at least one subsequent position wherein the jaw members cooperate to grasp tissue therebetween, each jaw member defining a longitudinal axis;

each of said jaw members including an electrically conductive sealing surface which communicates electrosurgical energy through tissue held therein;

at least one of the jaw members including a knife slot defined along a length thereof;

a knife blade reciprocally disposed in the knife slot for deployment therefrom, the knife blade defining a camming surface opposite a cutting edge thereof, wherein the knife blade defines a cutting edge that is oriented substantially parallel to the longitudinal axis of the respective jaw member; and a cutting mechanism for selectively actuating the knife blade from a first position wherein the knife blade is disposed at least substantially entirely within the knife slot of one jaw member to at least one subsequent position wherein the knife blade is at least partially deployed from the knife slot of the same jaw member, wherein the camming surface of the knife blade engages a corresponding camming surface formed in the slot of the jaw member to effectuate displacement of the knife blade between the first position and the at least one subsequent position to thereby slice tissue disposed between the jaw members.

9. The open electrosurgical forceps according to claim 8, wherein the cutting edge of the knife blade remains substantially parallel to the longitudinal axis of the respective jaw member during actuation thereof from the first position to the at least one subsequent position.

10. The open electrosurgical forceps according to claim 8, wherein as the knife blade is actuated from the first position to the at least one subsequent position the camming surface of the knife blade engages the camming surface of the slot formed in the jaw member to displace the knife blade in a direction substantially transverse to the longitudinal axis of the respective jaw member.

11. The open electrosurgical forceps according to claim 10, wherein as the knife blade is actuated from the first position to the at least one subsequent position the camming surface of the knife blade engages the camming surface of the slot formed in the jaw member to displace the knife blade in a direction having a longitudinal component of translation.

12. The open electrosurgical forceps according to claim 8, wherein the cutting mechanism selectively actuates the knife blade from a first distal position to at least one subsequent proximal position.

13. The open electrosurgical forceps according to claim 8, wherein the knife blade is fabricated from a material capable of transmitting compressive and tensile forces.

14. The open electrosurgical forceps according to claim 13, wherein each jaw member is arcuate.

15. The open electrosurgical forceps according to claim 14, wherein the slot formed in the respective jaw member is arcuate.

* * * * *